United States Patent
Ziniti et al.

(10) Patent No.: US 9,078,648 B2
(45) Date of Patent: Jul. 14, 2015

(54) INSTRUMENTS FOR DELIVERING TRANSFASCIAL SUTURES AND METHODS OF TRANSFASCIAL SUTURING

(75) Inventors: Donald E. Ziniti, Cumberland, RI (US); Roger E. Darois, Foster, RI (US); Kevin J. Ranucci, Warwick, RI (US); Richard M. Braga, North Easton, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 610 days.

(21) Appl. No.: 13/290,247

(22) Filed: Nov. 7, 2011

(65) Prior Publication Data

US 2013/0116710 A1    May 9, 2013

(51) Int. Cl.
A61B 17/04    (2006.01)
A61B 17/068    (2006.01)
(Continued)

(52) U.S. Cl.
CPC ......... *A61B 17/0469* (2013.01); *A61B 17/0482* (2013.01); *A61B 17/0485* (2013.01); *A61B 17/068* (2013.01); *A61B 2017/00818* (2013.01); *A61B 2017/0472* (2013.01); *A61B 2017/061* (2013.01); *A61B 2017/06009* (2013.01); *A61B 2017/06042* (2013.01); *A61B 2019/481* (2013.01)

(58) Field of Classification Search
CPC ........... A61B 17/0469; A61B 17/0482; A61B 17/0485; A61B 17/068; A61B 2017/0472; A61B 2017/06009; A61B 2017/06042; A61B 2017/061; A61B 2017/008181; A61B 2019/481
USPC ......... 606/139, 142, 144, 145, 148, 232, 113, 606/151, 153
See application file for complete search history.

(56) References Cited

U.S. PATENT DOCUMENTS

| 4,235,238 A | 11/1980 | Ogiu et al. |
| 4,696,300 A | 9/1987 | Anderson |

(Continued)

FOREIGN PATENT DOCUMENTS

| DE | 197 07 851 A1 | 9/1998 |
| EP | 1 762 185 A1 | 3/2007 |

(Continued)

OTHER PUBLICATIONS

Final Office Action for U.S. Appl. No. 13/157,182, mailed Jul. 5, 2013 (13 pages).

(Continued)

*Primary Examiner* — Julian W Woo
*Assistant Examiner* — Lucas Paez
(74) *Attorney, Agent, or Firm* — Wolf, Greenfield & Sacks, P.C.

(57) ABSTRACT

An instrument for delivering a suture transfascially may include a handle, a shaft extending from the handle, and at least one needle that is moveable to an extended position beyond the end of the shaft. A suture may be delivered transfascially with the instrument. The instrument may include a suture catch associated with each needle for retaining and releasing a suture segment. A shield may be provided to shield the sharp end of each needle when it is moved to the extended position. A method of delivering a transfascial suture may include inserting an instrument into an abdominal cavity and deploying, from within the abdominal cavity, each needle through a soft tissue repair patch and then through at least part of the abdominal wall. A suture or suture segment may be advanced across the fascia with the at least one needle.

29 Claims, 24 Drawing Sheets

(51) Int. Cl.
  *A61B 17/00* (2006.01)
  *A61B 17/06* (2006.01)
  *A61B 19/00* (2006.01)

(56) References Cited

U.S. PATENT DOCUMENTS

| | | | |
|---|---|---|---|
| 4,935,027 A | 6/1990 | Yoon | |
| 5,222,508 A | 6/1993 | Contarini | |
| 5,281,237 A * | 1/1994 | Gimpelson | 606/144 |
| 5,290,217 A | 3/1994 | Campos | |
| 5,290,297 A | 3/1994 | Phillips | |
| 5,366,480 A | 11/1994 | Corriveau et al. | |
| 5,403,329 A | 4/1995 | Hinchcliffe | |
| 5,470,337 A | 11/1995 | Moss | |
| 5,500,000 A | 3/1996 | Feagin et al. | |
| 5,501,692 A | 3/1996 | Riza | |
| 5,618,290 A | 4/1997 | Toy et al. | |
| 5,626,614 A | 5/1997 | Hart | |
| 5,643,319 A | 7/1997 | Green et al. | |
| 5,713,910 A | 2/1998 | Gordon et al. | |
| 5,772,672 A | 6/1998 | Toy et al. | |
| 5,810,848 A | 9/1998 | Hayhurst | |
| 5,868,762 A | 2/1999 | Cragg et al. | |
| 5,904,692 A | 5/1999 | Steckel et al. | |
| 5,944,739 A | 8/1999 | Zlock et al. | |
| 5,964,773 A | 10/1999 | Greenstein | |
| 6,022,360 A | 2/2000 | Reimels et al. | |
| 6,210,416 B1 | 4/2001 | Chu et al. | |
| 6,287,317 B1 | 9/2001 | Makower et al. | |
| 6,293,952 B1 | 9/2001 | Brosens et al. | |
| 6,500,184 B1 | 12/2002 | Chan et al. | |
| 6,506,197 B1 | 1/2003 | Rollero et al. | |
| 6,551,333 B2 | 4/2003 | Kuhns et al. | |
| 6,565,590 B2 | 5/2003 | Kieturakis et al. | |
| 6,596,014 B2 | 7/2003 | Levinson et al. | |
| 6,626,930 B1 | 9/2003 | Allen et al. | |
| 6,638,286 B1 | 10/2003 | Burbank et al. | |
| 6,821,285 B2 | 11/2004 | Laufer et al. | |
| 6,966,916 B2 | 11/2005 | Kumar | |
| 7,021,316 B2 | 4/2006 | Leiboff | |
| 7,381,210 B2 | 6/2008 | Zarbatany et al. | |
| 7,442,198 B2 | 10/2008 | Gellman et al. | |
| 7,722,629 B2 | 5/2010 | Chambers | |
| 7,722,633 B2 | 5/2010 | Laufer et al. | |
| 7,740,638 B2 | 6/2010 | Hyde | |
| 7,846,179 B2 | 12/2010 | Belef et al. | |
| 7,879,048 B2 * | 2/2011 | Bain et al. | 606/144 |
| 7,918,868 B2 | 4/2011 | Marshall et al. | |
| 7,942,886 B2 * | 5/2011 | Alvarado | 606/144 |
| 7,959,640 B2 | 6/2011 | Kantsevoy et al. | |
| 8,512,375 B2 | 8/2013 | Torrie et al. | |
| 8,702,753 B2 | 4/2014 | Mikkaichi et al. | |
| 8,790,356 B2 | 7/2014 | Darois et al. | |
| 2001/0021856 A1 | 9/2001 | Bolduc et al. | |
| 2002/0019649 A1 | 2/2002 | Sikora et al. | |
| 2003/0045891 A1 | 3/2003 | Yamamoto et al. | |
| 2003/0105489 A1 | 6/2003 | Eichhorn et al. | |
| 2004/0092969 A1 | 5/2004 | Kumar | |
| 2004/0133238 A1 | 7/2004 | Cerier | |
| 2005/0021055 A1 | 1/2005 | Toubia et al. | |
| 2005/0033363 A1 | 2/2005 | Bojarski et al. | |
| 2005/0049635 A1 | 3/2005 | Leiboff | |
| 2006/0020247 A1 | 1/2006 | Kagan et al. | |
| 2006/0020273 A1 | 1/2006 | Hatch et al. | |
| 2006/0025819 A1 | 2/2006 | Nobis et al. | |
| 2006/0069399 A1 | 3/2006 | Weisel et al. | |
| 2006/0116718 A1 | 6/2006 | Leiboff | |
| 2006/0142784 A1 | 6/2006 | Kontos | |
| 2006/0178680 A1 | 8/2006 | Nelson et al. | |
| 2006/0265009 A1 | 11/2006 | Bonutti | |
| 2006/0265011 A1 | 11/2006 | Bonutti | |
| 2006/0293709 A1 | 12/2006 | Bojarski et al. | |
| 2007/0049970 A1 | 3/2007 | Belef et al. | |
| 2007/0073319 A1 | 3/2007 | Mikkaichi et al. | |
| 2007/0118153 A1 | 5/2007 | Funamura et al. | |
| 2007/0149987 A1 | 6/2007 | Wellman et al. | |
| 2007/0185532 A1 | 8/2007 | Stone et al. | |
| 2007/0191886 A1 | 8/2007 | Dejima et al. | |
| 2007/0276414 A1 | 11/2007 | Nobles | |
| 2007/0293876 A1 | 12/2007 | Abe et al. | |
| 2008/0091219 A1 | 4/2008 | Marshall et al. | |
| 2008/0114378 A1 | 5/2008 | Matsushita | |
| 2008/0114399 A1 | 5/2008 | Bonutti | |
| 2008/0140092 A1 | 6/2008 | Stone et al. | |
| 2008/0154286 A1 | 6/2008 | Abbott et al. | |
| 2008/0255591 A1 | 10/2008 | Harada et al. | |
| 2008/0294001 A1 | 11/2008 | Surti | |
| 2009/0023997 A1 | 1/2009 | Stokes et al. | |
| 2009/0062817 A1 | 3/2009 | Suzuki et al. | |
| 2009/0069823 A1 | 3/2009 | Foerster et al. | |
| 2009/0088780 A1 | 4/2009 | Shiono et al. | |
| 2009/0118734 A1 | 5/2009 | Bhatnagar et al. | |
| 2009/0171140 A1 | 7/2009 | Chu | |
| 2009/0216253 A1 | 8/2009 | Bell et al. | |
| 2009/0228041 A1 | 9/2009 | Domingo | |
| 2009/0326566 A1 | 12/2009 | Alvarado | |
| 2010/0030236 A1 | 2/2010 | Hayashi et al. | |
| 2010/0069930 A1 | 3/2010 | Roslin et al. | |
| 2010/0106166 A1 | 4/2010 | Cropper et al. | |
| 2010/0121353 A1 | 5/2010 | Marshall et al. | |
| 2010/0234854 A1 | 9/2010 | Abbott et al. | |
| 2010/0249809 A1 | 9/2010 | Singhatat et al. | |
| 2010/0262166 A1 | 10/2010 | Boraiah et al. | |
| 2010/0292712 A1 | 11/2010 | Nering et al. | |
| 2010/0292719 A1 | 11/2010 | Ducharme | |
| 2010/0324573 A1 | 12/2010 | Toubia et al. | |
| 2011/0082472 A1 | 4/2011 | Harris et al. | |
| 2012/0035626 A1 | 2/2012 | Chu | |
| 2012/0143220 A1 | 6/2012 | Morgan et al. | |
| 2012/0143221 A1 | 6/2012 | Weisel et al. | |

FOREIGN PATENT DOCUMENTS

| | | | |
|---|---|---|---|
| EP | 1 769 749 A1 | 4/2007 | |
| EP | 1 808 134 A2 | 7/2007 | |
| JP | 5-161655 A | 6/1993 | |

OTHER PUBLICATIONS

Final Office Action for U.S. Appl. No. 13/290,222 mailed Dec. 4, 2013 (16 pages).
Office Action for U.S. Appl. No. 13/157,172 mailed on Oct. 18, 2013 (9 pages).
Office Action for U.S. Appl. No. 13/416,740, mailed Oct. 25, 2013 (13 pages).
Office Action for U.S. Appl. No. 13/157,155, mailed Jan. 3, 2014 (18 pages).
Office Action for U.S. Appl. No. 13/157,172 mailed on Apr. 3, 2014 (11 pages).
International Preliminary Report on Patentability for International Application No. PCT/US2012/063699 mailed May 13, 2014 (6 pages).
Office Action for U.S. Appl. No. 13/157,182, mailed Aug. 5, 2014 (12 pages).
Office Action for U.S. Appl. No. 13/157,172, mailed Aug. 12, 2014 (13 pages).
International Search Report and Written Opinion of the International Searching Authority for International Application No. PCT/US12/63699, mailed Apr. 2, 2013 (10 pages).
Office Action for U.S. Appl. No. 13/157,182, mailed on Oct. 10, 2012 (12 pages).
Office Action for U.S. Appl. No. 13/290,222, mailed on Apr. 2, 2013 (12 pages).
Office Action for U.S. Appl. No. 13/157,172 mailed on Feb. 12, 2015 (8 pages).
Final Office Action for U.S. Appl. No. 13/157,182, mailed Feb. 25, 2015 (14 pages).
Final Office Action for U.S. Appl. No. 13/157,155, mailed Oct. 14, 2014 (23 pages).
Office Action for U.S. Appl. No. 13/290,222, mailed on Oct. 31, 2014 (19 pages).
Office Action for U.S. Appl. No. 13/290,236, mailed Nov. 6, 2014 (7 pages).

* cited by examiner

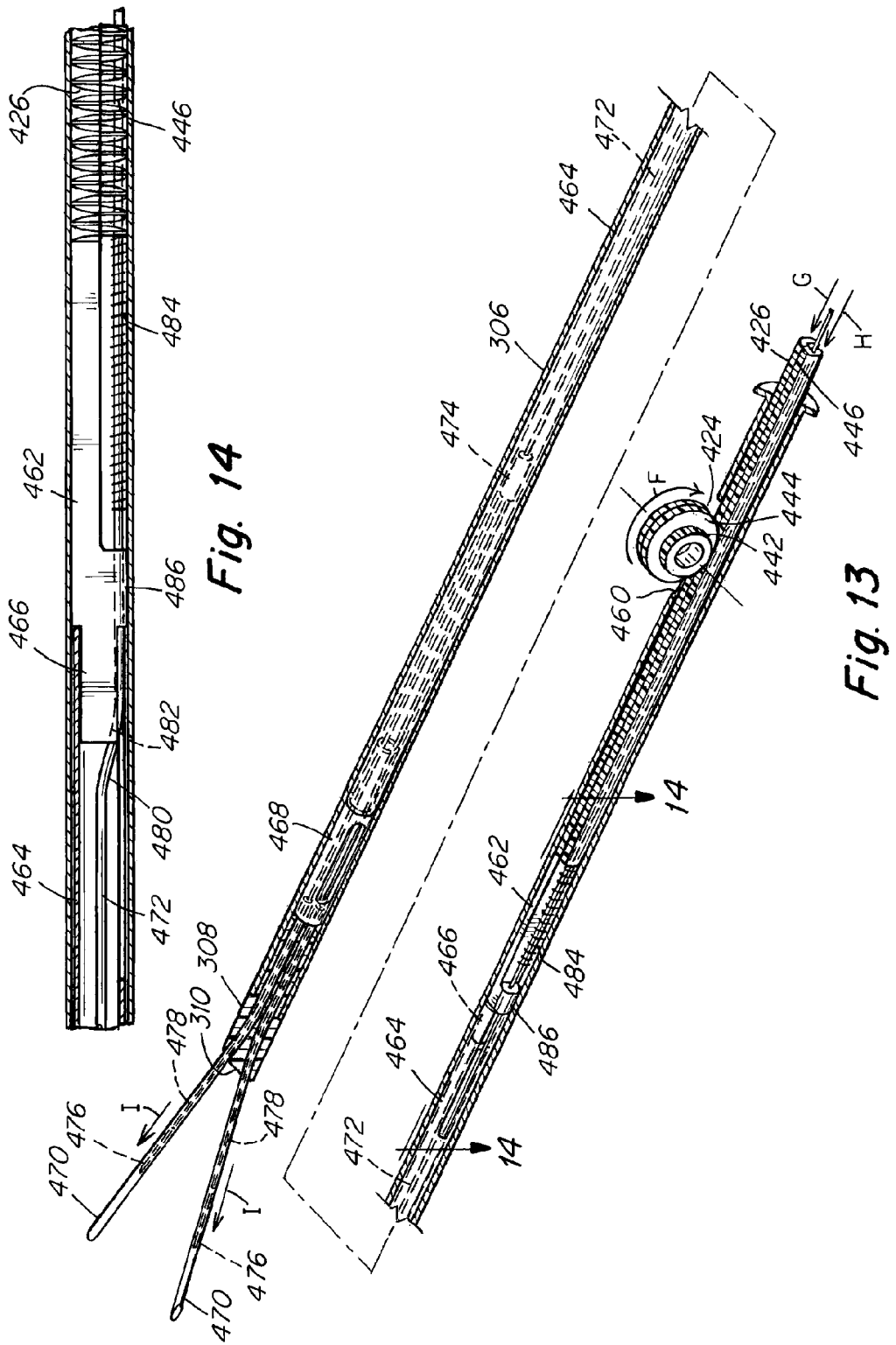

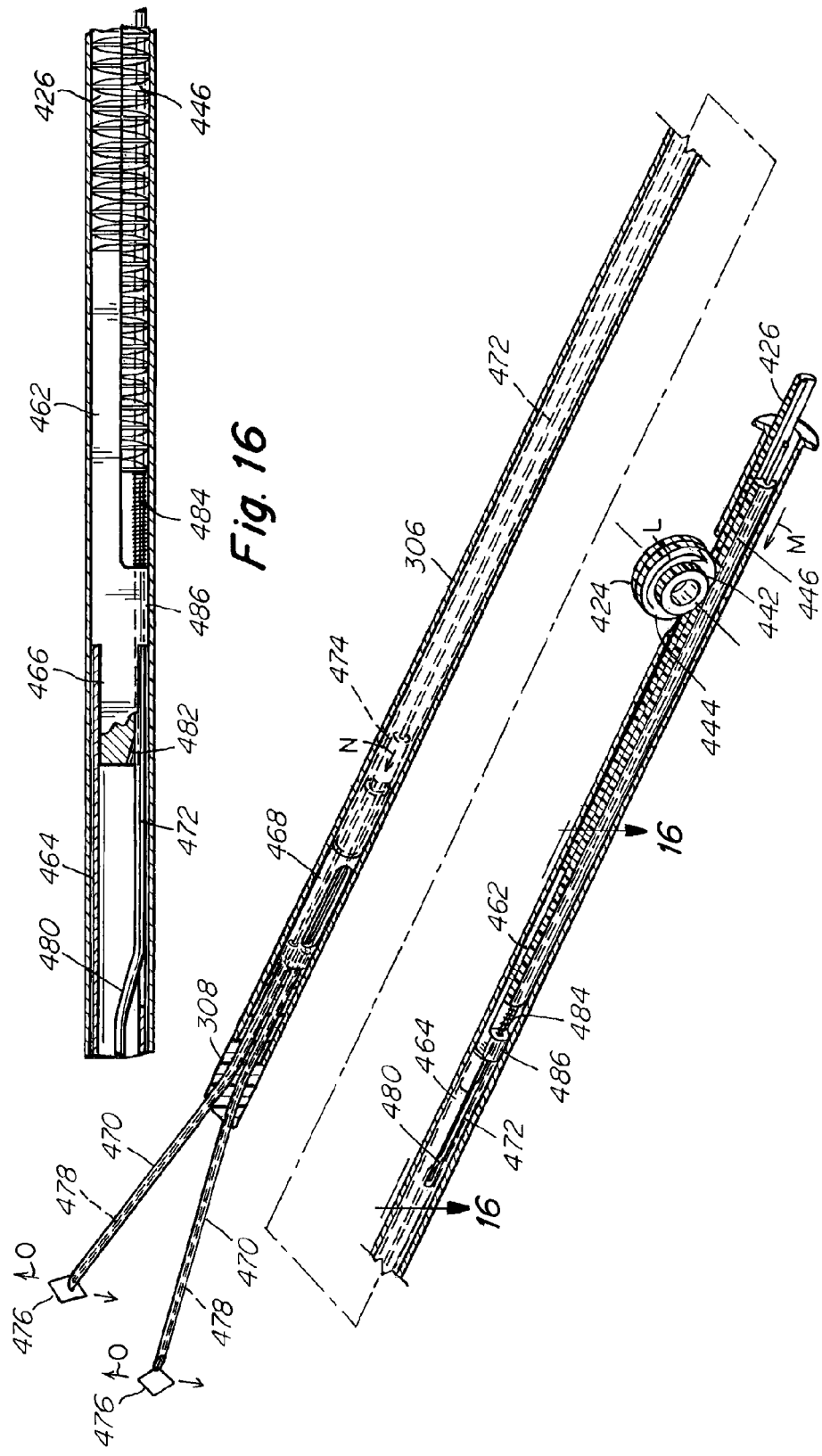

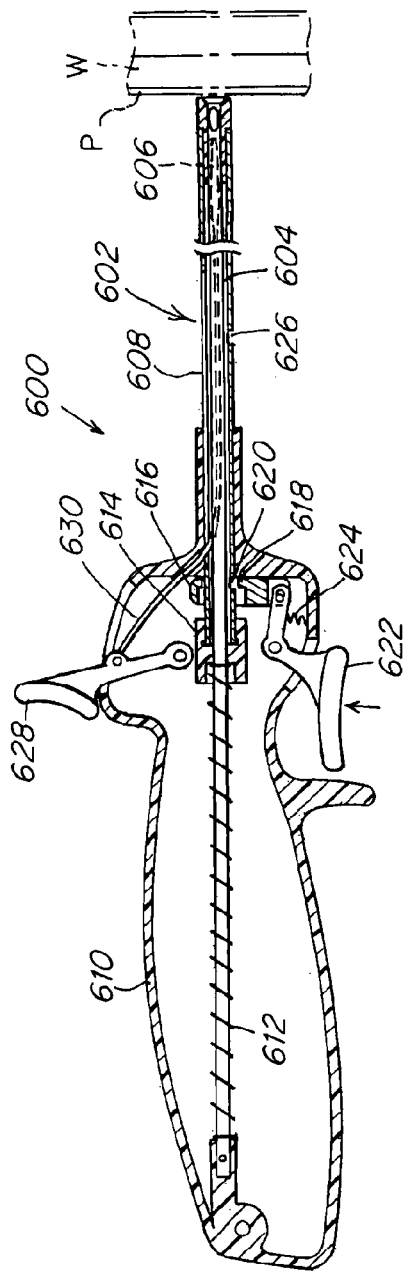
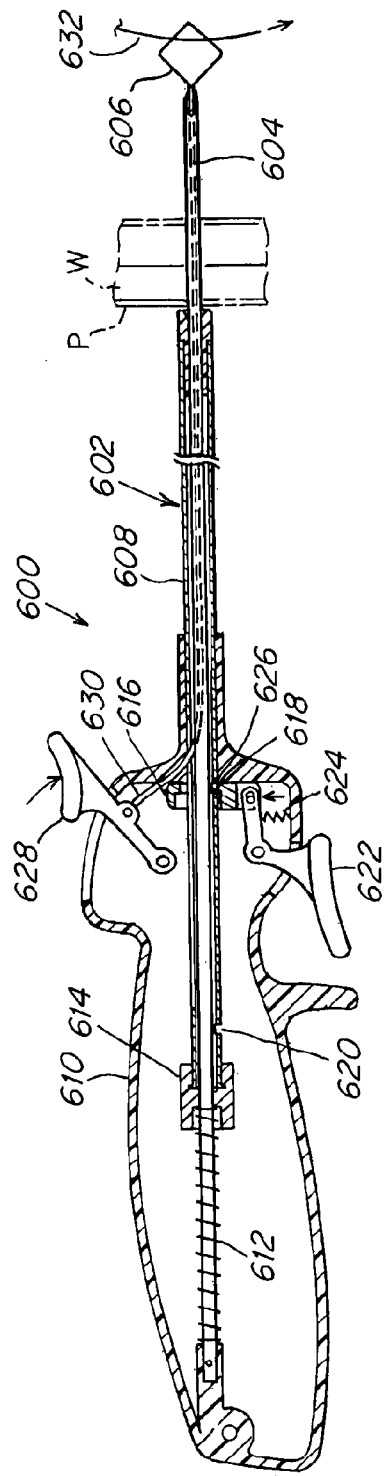
Fig. 18A
Fig. 18B

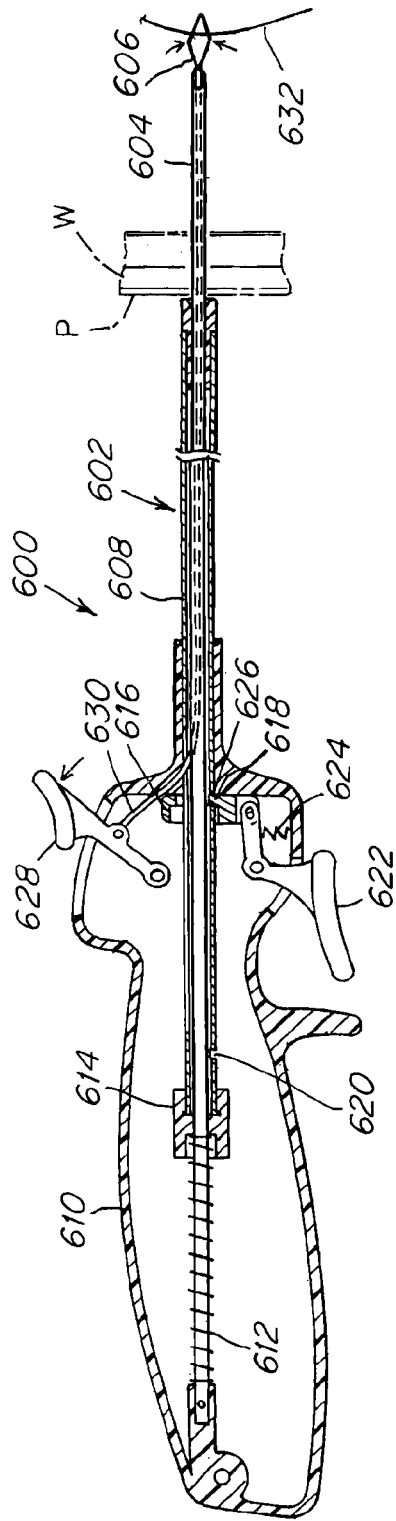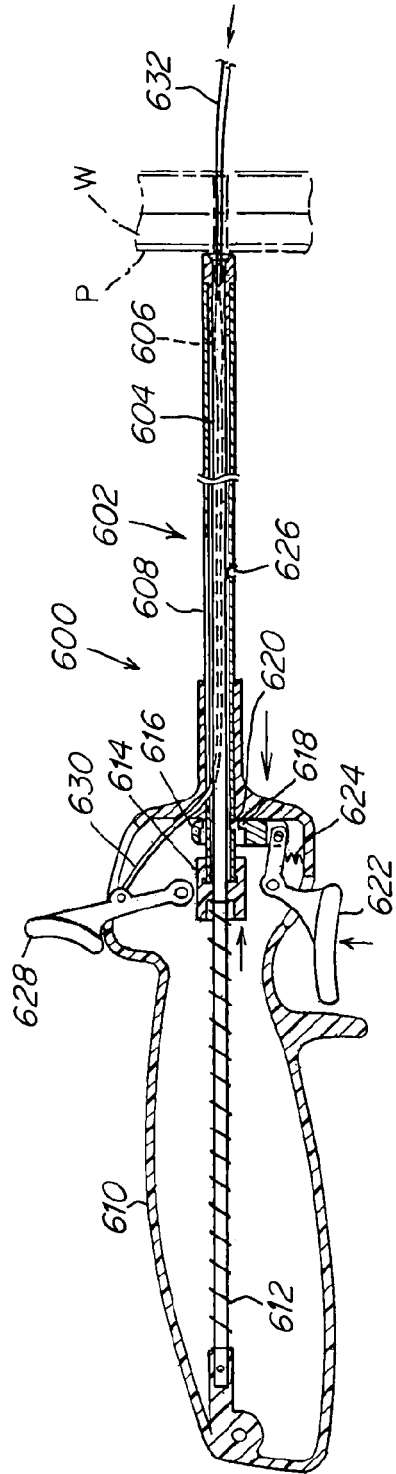
Fig. 18C
Fig. 18D

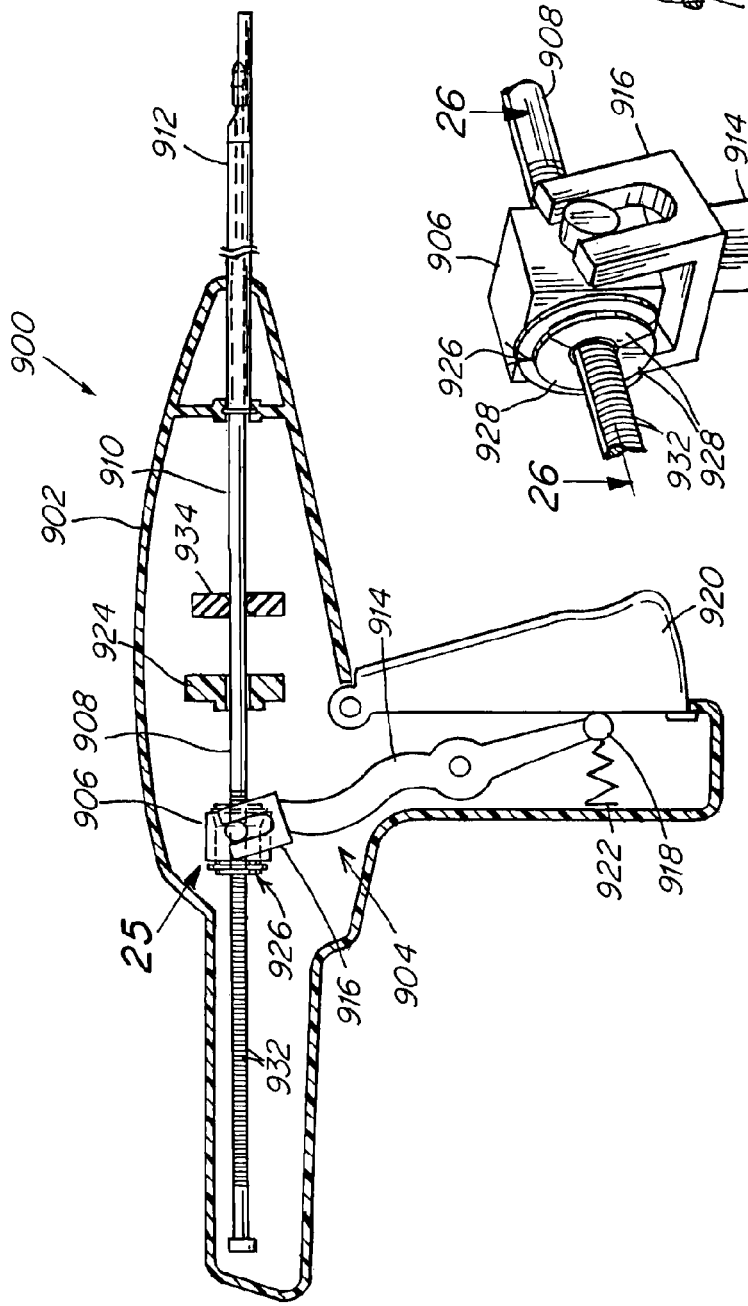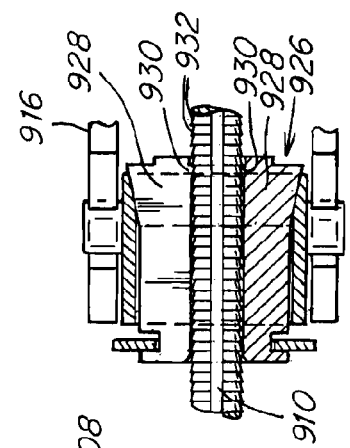
Fig. 24
Fig. 25
Fig. 26

INSTRUMENTS FOR DELIVERING TRANSFASCIAL SUTURES AND METHODS OF TRANSFASCIAL SUTURING

FIELD

The invention relates to instruments for delivering transfascial sutures and to methods of transfascial suturing.

BACKGROUND

Ventral hernia repair routinely involves placement of a soft tissue repair prosthetic, typically in the form of a patch, across an abdominal wall defect. In a laparoscopic procedure, or other minimally invasive approach, the patch is reduced in size and delivered through a narrow cannula or incision into the abdominal cavity where it then is returned to an expanded shape and deployed against the abdominal wall. Sutures may be applied through a partial, if not full, thickness of the abdominal wall (i.e., transfascial suturing). Additionally, or alternatively, tacks, screws, coils or other fasteners may be placed through the patch into just the innermost layers of the abdominal wall, such as the peritoneum and posterior fascia.

A conventional approach for transfascial suture delivery, as shown in FIG. 1, proceeds from outside of the patient. Sutures are pre-tied at spaced locations 100 about a patch 102 periphery, with pairs of suture tails 104 extending from each knot. It is these tails that will bridge the fascia and be secured together to form the transfascial suture fixation. The patch, pre loaded with sutures, is collapsed and delivered into the abdominal cavity.

A suture passer instrument 106 is inserted, from outside of the patient, through the abdominal wall 108 and into the abdominal cavity in the approximate location of a particular suture tail pair. The suture passer includes a jaw or other grasper type arrangement which is operated within the cavity to capture one of the suture tails. The suture passer is retracted back through and out of the abdominal wall, drawing the suture tail exteriorly of the abdominal cavity. A hemostat or other clamp is applied to the exposed suture tail, preventing slippage of the suture tail back into the abdominal cavity. The suture passer is inserted again through the abdominal wall, creating a new puncture adjacent the first puncture, and operated to grab the remaining suture tail. The suture passer is pulled outwardly from the abdominal cavity, retrieving the second suture tail which also can be clamped against the anterior fascia. This standard transfascial suturing technique, approached from outside of the abdominal cavity, is repeated until all of the suture tail pairs have been transfascially deployed and tied together, typically at small skin incisions such that the tied knots are in the subcutaneous space.

SUMMARY

One aspect of the invention is an instrument for delivering a transfascial suture. The instrument comprises a handle, an elongated shaft extending from the handle, at least one needle moveable to at least one extended position beyond a distal end of the shaft, at least one suture catch movable to an extended position beyond the distal end of the shaft, and a drive mechanism adapted to advance the at least one needle and/or the at least one suture catch to an extended position. The at least one needle has a sharp end adapted to pierce a soft tissue repair prosthetic and abdominal wall tissue. The suture catch is adapted to retain and release a suture segment.

Another aspect of the invention is an instrument for delivering a transfascial suture. The instrument comprises a handle, an elongated shaft extending from the handle, at least one needle moveable to at least one extended position beyond a distal end of the shaft, at least one probe that is extendable beyond the sharp end of the at least one needle, and a drive mechanism adapted to advance the at least one needle and/or the probe to an extended position. The at least one needle has a sharp end adapted to pierce a soft tissue repair prosthetic and abdominal wall tissue.

Another aspect of the invention is an instrument for delivering a transfascial suture. The instrument comprises a handle, an elongated shaft extending from the handle, at least one needle moveable to an extended position beyond a distal end of the shaft, and a drive mechanism adapted to advance the at least one needle to the at least one extended position. The at least one needle has a sharp end adapted to pierce a soft tissue repair prosthetic and abdominal wall tissue. The instrument also comprises at least one shield adapted to shield the sharp end of the at least one needle from contact therewith when the needle is moved to the extended position. At least one of the shield and the needle is movable relative to the other of the shield and the needle between a first position to shield the sharp end and a second position to expose the sharp end.

Another aspect of the invention is an instrument for delivering a transfascial suture. The instrument comprises a handle, an elongated shaft extending from the handle, first and second suture guides moveable to at least one extended position beyond a distal end of the shaft, and a drive mechanism adapted to advance the first and second suture guides to the at least one extended position. Each of the first and second suture guides has a sharp end adapted to pierce a soft tissue repair prosthetic and abdominal wall tissue. Each of the first and second suture guides is adapted to guide a suture therealong. The instrument also comprises a suture guide support adapted to guide the suture from the first suture guide to the second suture guide.

Another aspect of the invention is an instrument for delivering a transfascial suture. The instrument comprises a handle, an elongated shaft extending from the handle, at least one needle moveable to a plurality of extended positions beyond a distal end of the shaft that differ from each other, and a drive mechanism adapted to advance the at least one needle to the plurality of extended positions in response to multiple actuations of the drive mechanism. The at least one needle has a sharp end adapted to pierce a soft tissue repair prosthetic and abdominal wall tissue.

Another aspect of the invention is an instrument for delivering a transfascial suture. The instrument comprises a handle, a needle having a sharp end adapted to pierce a soft tissue repair prosthetic and abdominal wall tissue, and an elongated shaft extending from the handle. The shaft is movable from an extended position that covers the sharp end of the needle to at least one retracted position that exposes the sharp end of the needle. The instrument also comprises a shaft locking mechanism adapted to lock the shaft in at least one position relative to the sharp end of the needle.

Another aspect of the invention is a method of delivering a transfascial suture comprising acts of (a) inserting an instrument into an abdominal cavity, the instrument including at least one needle having a sharp distal end adapted to pierce a soft tissue repair prosthetic and abdominal wall tissue; (b) delivering a suture from outside the abdominal cavity through abdominal wall tissue and into the abdominal cavity at a first location using the instrument from within the abdominal cavity; and (c) after act (b), delivering the suture from inside the abdominal cavity through abdominal wall tissue and outside the abdominal cavity at a second location spaced from the first location using the instrument from within the abdominal cavity.

Another aspect of the invention is a method of delivering a transfascial suture comprising acts of (a) inserting a suturing instrument into an abdominal cavity, the suturing instrument including a needle with a sharp end adapted to pierce abdominal wall tissue; (b) after act (a), advancing the needle through the abdominal wall at a first location and extending the sharp end of the needle outside the abdominal cavity; (c) after act (b), loading a suture on the suturing instrument outside the abdominal cavity; and (d) after act (c), drawing the suture through the abdominal wall and into the abdominal cavity at the first location.

Another aspect of the invention is a method of delivering a transfascial suture comprising acts of (a) inserting a suturing instrument into an abdominal cavity, the suturing instrument including at least one needle with a sharp end adapted to pierce abdominal wall tissue; (b) advancing the at least one needle from inside the abdominal cavity through the abdominal wall to outside the abdominal cavity; (c) shielding the sharp end of the at least one needle from contact therewith outside the abdominal cavity with the needle extending through the abdominal wall; and (d) passing a suture through the abdominal wall with the suturing instrument.

Another aspect of the invention is a method of delivering a transfascial suture comprising acts of (a) inserting a suturing instrument into an abdominal cavity, the suturing instrument including at least one needle having a sharp end adapted to pierce a soft tissue repair prosthetic and abdominal wall tissue, the suturing instrument adapted to pass a suture through the abdominal wall; (b) advancing the at least one needle from inside the abdominal cavity through a portion of the abdominal wall; (c) identifying the location of the at least one needle in the abdominal wall via skin tenting and/or skin palpation; and (d) following act (c), passing a suture through the abdominal wall with the suturing instrument.

BRIEF DESCRIPTION OF DRAWINGS

The foregoing and other objects and advantages of the invention will be appreciated more fully from the following drawings, wherein like reference characters designate like features, in which:

FIGS. 10-16 are partial sectional illustrations of a drive mechanism for the instruments of FIGS. 2-9B;

FIGS. 18A-18D are illustrations of an instrument for transfascial delivery of a suture with a retractable shaft and a suture catch;

FIGS. 24-27 are partial sectional illustrations of a drive mechanism for an instrument for transfascial delivery of a suture;

DETAILED DESCRIPTION

Figure 1:
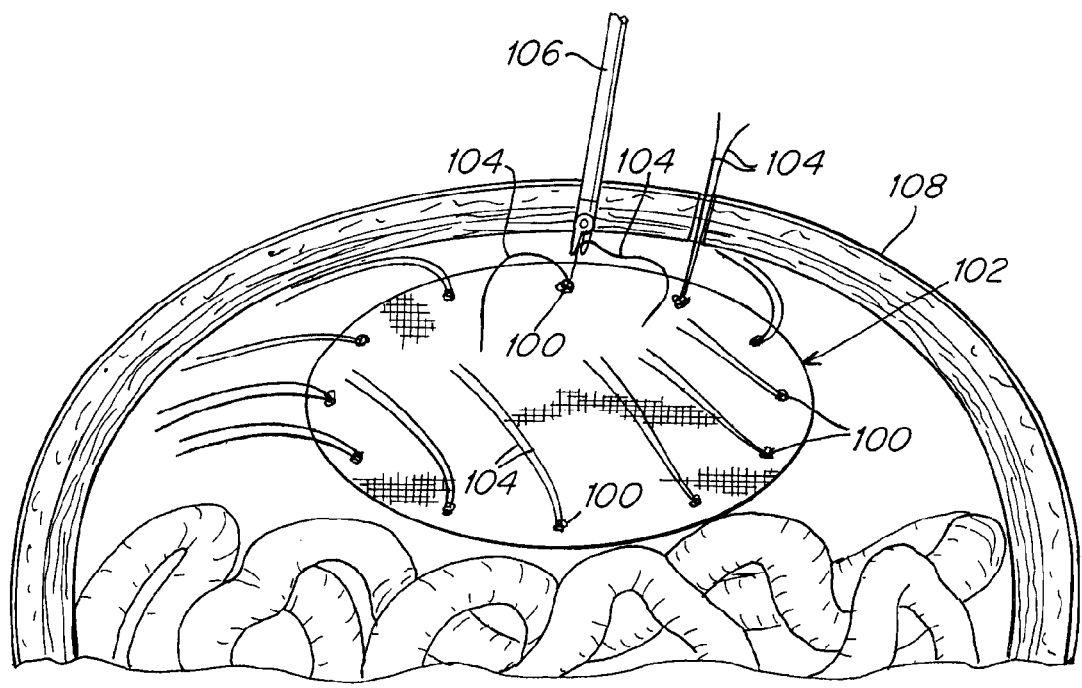
FIG. 1 is an illustration of a conventional transfascial suture delivery.

Various aspects of the invention are described below and/or shown in the drawings. These aspects of the invention may be used alone and/or in any suitable combination with each other. Aspects of the invention are not limited in any way by the illustrative embodiments shown and described herein.

Embodiments of the invention are described in connection with instruments for transfascial delivery of one or more sutures, and methods of delivering a transfascial suture. These instruments and methodologies are particularly configured for transfascial delivery of suture from within the abdominal cavity, rather than in the traditional manner of pulling suture across the fascia in an approach from outside of the patient. Such instruments and techniques may be applied independently or in conjunction with other approaches, such as those involving mechanical fastener-type fixation. Although disclosed in connection with a repair of a ventral hernia, the invention is not so limited and has other applications as should be apparent to one of skill in the art.

An instrument for transfascial delivery of suture may include an actuating handle, an elongated shaft extending from the handle, and a suture passer for advancing a suture across the fascia. The shaft may be relatively rigid or flexible, fixed or moveable relative to the handle, and may be sized to fit through a narrow cannula, such as a 5 mm cannula or even smaller—although the outer diameter of the shaft is not necessarily a limitation of the invention.

The suture passer may include one or a pair of needles or other tissue piercing elements, each with an end configured for piercing tissue and/or a soft tissue repair prosthetic, such as a ventral hernia patch. Each needle or tissue piercing element may be arranged to move in either one full stroke through the abdominal wall or in multiple partial strokes to control penetration through the abdominal wall. A pair of needles may be arranged to move simultaneously or, instead, in sequence, and may be driven by a single or a dual actuating arrangement (e.g., one trigger or two triggers).

For some transfascial suturing procedures, it may be desirable to employ a transfascial suturing instrument that may be loaded with a suture by a surgeon or other user either prior to or during a transfascial suturing procedure. Such a device allows a surgeon to select and use any of various types of suture material when performing transfascial suturing. For example, and without limitation, a surgeon may wish to perform transfascial suturing using various sized sutures, non-absorbable sutures, absorbable sutures or even a combination of non-absorbable and absorbable sutures for a particular procedure.

The suture passer may include one or a pair of suture catches configured for loading, retaining and releasing a suture segment to facilitate advancement of a suture across the fascia. Each catch may be moveable to an extended position beyond a distal end of the shaft to load and release a suture segment. Each catch may be operatively associated with a needle or tissue piercing element so that a suture may be advanced across fascial tissue by moving each needle.

The catch may include a resilient frame that opens to receive and release a suture when extended from a needle and/or the shaft and collapses to retain a suture when retracted into the needle and/or the shaft. Alternatively, and without limitation, the catch may include a groove or other feature provided on the needle that can be opened to receive and release a suture and closed to retain a suture. A suture may be either preloaded or loaded on the instrument by a user using a suture catch.

Using a single-needle arrangement from within an abdominal cavity, a suture associated with the needle may be delivered from outside the abdominal cavity, through fascial tissue and then a ventral hernia patch and into the abdominal cavity at a first location, and subsequently delivered through the ventral hernia patch and then fascial tissue and out of the abdominal cavity at a second location. Delivering suture in this manner results in first and second suture segments extending through the ventral hernia patch and the fascial tissue with an intermediate suture segment extending between the first and second suture segments and remaining in the abdominal cavity internal of the ventral hernia patch.

Using a dual-needle arrangement, a suture may be arranged so that a first suture segment is associated with a first needle and a second suture segment is associated with a second needle, with an intermediate suture segment extending between the two. So arranged, deployment of the pair of needles will deliver both suture segments from within the abdominal cavity through a ventral hernia patch and then through fascial tissue, with the intermediate segment remaining in the abdominal cavity internal of the ventral repair patch.

The portions of the first and second suture segments extending through and beyond the patch and fascial tissue, referred to as suture tails or suture segment tails, may be joined, such as by tying. Prior to joining, the suture segments may be pulled to draw the intermediate segment against the ventral repair patch.

A suture force distributing member may be provided along the intermediate segment of the suture, so that the force distributing member contacts the ventral repair patch when the suture tails are drawn away from the abdominal cavity and/or secured together. The suture force distributing member may be fixed in position on the intermediate segment or may 'float' along the intermediate segment.

The instrument may include one or a pair of tissue probes that are extendable beyond the distal end of the shaft, and preferably the sharp end of each needle. Each probe may have a blunt end to reduce the incidence of an inadvertent needle stick when the probe is extended beyond the end of the needle. For example, and without limitation, the probe may be used to help locate the position of a needle, via skin tenting or palpation, by extending the probe beyond the end of the needle and through fascial tissue, after the needle has been partially advanced through the abdominal wall from within the abdominal cavity.

The instrument may include one or more shields to guard or isolate the sharp end of each needle from contact therewith when the needle is in an extended position. The sharp end of the needle may be guarded or exposed by moving the shield relative to the needle, moving the needle relative to the shield, or a combination of movements between the shield and needle.

The instrument may be configured as a reusable device, a disposable device, or a hybrid including a reusable aspect and a disposable aspect. A safety mechanism may be provided to prevent firing of the needle until the safety mechanism is released by a user. The instrument and suture preferably will be sterilized prior to transfascial suturing.

An instrument 200 for delivering a transfascial suture using either an inside-out technique or an outside-in technique is shown in FIGS. 2-6D. The instrument may be used within the abdominal cavity to pass a suture in either direction through the abdominal wall. The instrument may include a suture passer 202 for passing a suture through the abdominal wall at a first location, either into the abdominal cavity from outside a patient's body or from inside the abdominal cavity to outside the body, and passing the suture through the abdominal wall at a second location, either from inside the abdominal cavity to outside the body or into the abdominal cavity from outside the body.

The suture passer may include a needle 204, or other tissue piercing element, and a suture catch 206. The suture passer 202 may be housed within an elongated shaft 208 and may be operated with a needle drive mechanism included within and actuatable at a handle provided at a proximal end of the shaft. The suture catch may be located within the needle and operated with a catch drive mechanism that is also included within and actuatable at the handle. The needle and catch may be actuated with the same or different drive mechanisms.

As shown, the suture catch 206 is adapted to be collapsed into a closed position (FIGS. 3-4) to grip a portion of a suture and to be expanded into an open position (FIGS. 2 and 5) to receive and/or release the suture. The suture catch is configured to be advanceable from the distal tip of the needle 204 for receiving and/or releasing a suture and retractable into the needle for gripping and providing transport of the suture in and out of the abdominal cavity. In one embodiment, the suture catch 206 may include a resilient frame that is adapted to expand to the open position when extended beyond and no longer confined within the needle. The frame is adapted to coact with the distal end of the needle and collapse into the closed position as the catch is retracted into the needle. The frame may be supported at a distal end of a drive wire 210, such as a hypotube, that is coupled to a drive mechanism at the handle for operating the catch.

Figure 3:
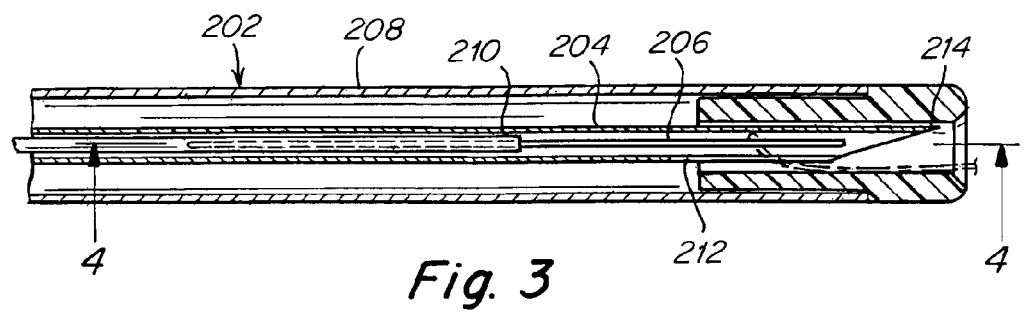
Figure 4:
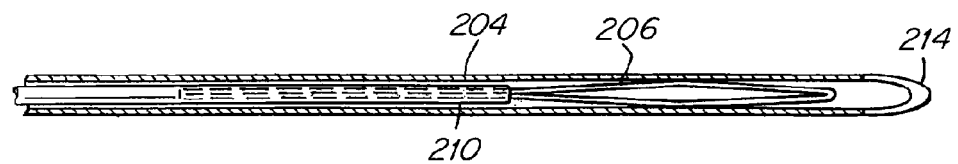

The needle may be provided with a relief adapted to receive a portion of the suture as it is drawn into the needle with the catch. In one embodiment as shown in FIG. 3, the needle may include a longitudinal slot 212 that extends in a proximal direction from the needle tip and along a portion of the needle. The distal end of the slot is open to receive suture material that is gripped by the catch and drawn into the needle. As shown, the slot 212 may be located along a portion of the needle opposite the sharpened tip 214. It is to be appreciated that other types of suture relief may be employed, if desired, and such relief may be located at any suitable portion of the needle as should be apparent to one of skill in the art.

Figure 2:
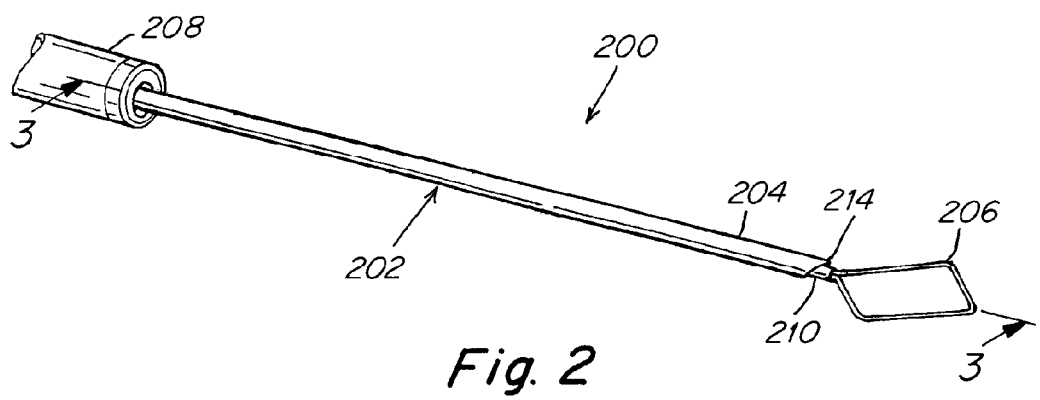
FIGS. 2-6D are illustrations of an instrument for transfascial delivery of a suture with an expandable suture catch.
Figure 5:
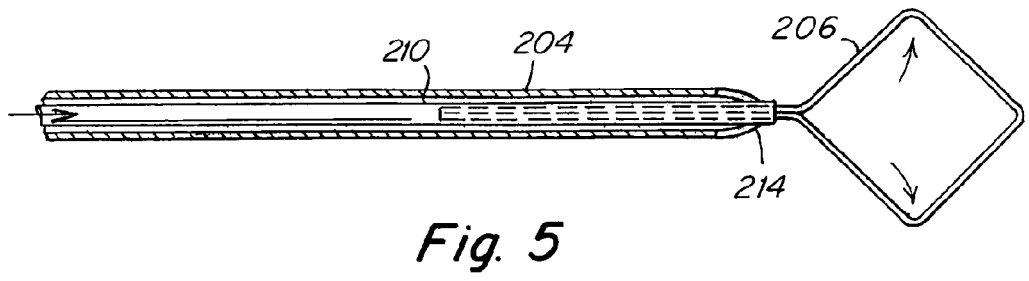

As shown in FIGS. 2 and 5, the catch 206 may have a generally diamond or square shape in the open position that collapses into a slender configuration (FIG. 4) for gripping the suture, although other shapes may be employed as should be apparent to one of skill. The catch may be formed of any suitable material including, but not limited to, spring steel or plastic, that provides the frame with flexibility and/or resilient characteristics, and using any suitable process including, but not limited to, bending or molding, as should be apparent to one of skill in the art.

As shown, the catch 206 is located adjacent the needle tip when advanced from the end of the needle for loading and releasing suture. If desired, the suture passer may include a shield, such as a shield similar to that described further below, to cover and/or isolate the needle tip as a suture is loaded into and unloaded from the catch.

An illustrative method of delivering a transfascial suture using the instrument 200 of FIGS. 2-5 will be described in connection with FIGS. 6A-6D.

Figure 6A:
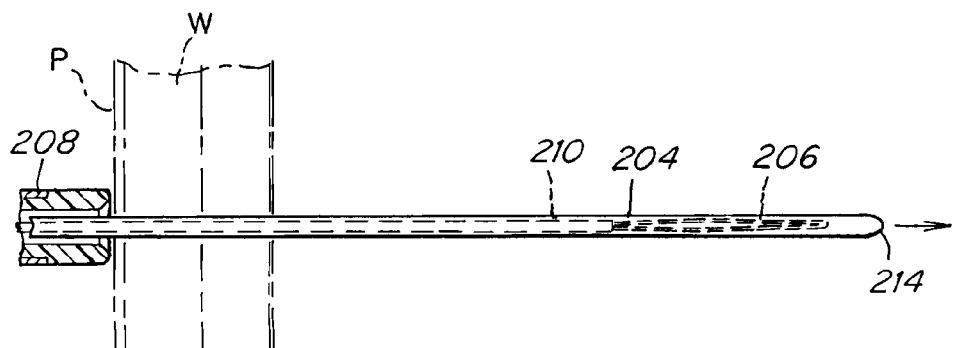

The instrument may be inserted into the abdominal cavity in a sharps-free condition with the suture passer 202 retracted within the shaft 208, such as shown in FIG. 3. As shown in FIG. 6A, following placement of the instrument within the abdominal cavity at a desired location against the abdominal wall patch P and/or fascia W, the suture passer 202 is extended from the distal end of the shaft with the needle tip exposed to penetrate the abdominal wall W and skin. In one embodiment, the suture passer may be extended from the shaft with a drive mechanism provided in the handle that employs a multi-stage and/or partial stroke actuation. For example, and without limitation, the drive mechanism may be adapted to extend the suture passer in partial strokes to incrementally penetrate the abdominal wall with each successive actuation. The drive mechanism continues to be actuated until the needle 204 either exits the skin or produces skin tenting. If desired, actuation of the device may be paused, either when skin tenting is observed or to otherwise perform palpation of the abdominal wall, so that the surgeon may make a skin incision prior to needle penetration, thereby lowering the force that may be necessary for the needle to penetrate the skin. Actuation of the drive mechanism continues until the suture passer is fully extended to present the suture catch outside the abdominal cavity.

Figure 6B:
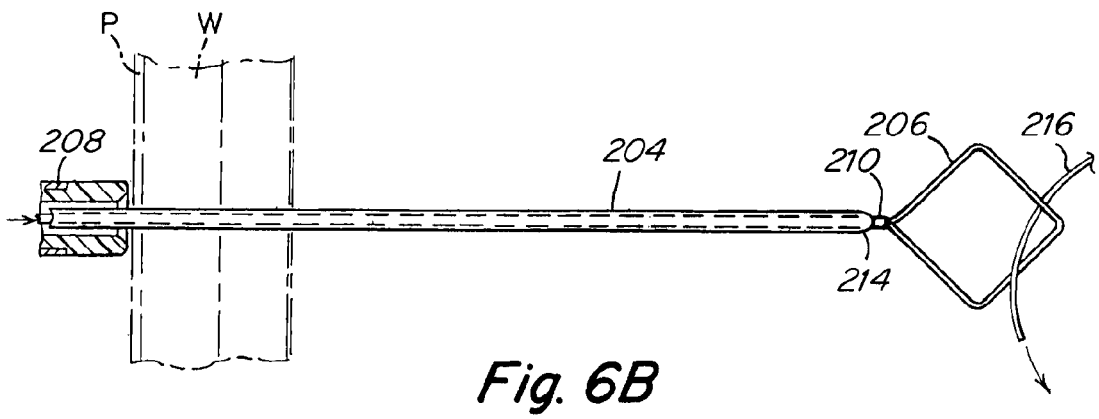

As shown in FIG. 6B, further actuation of the device, which may involve engagement of the same or different mechanism, extends the suture catch 206. As shown, the suture catch may be arranged to extend in a distal direction from the needle 204, although the catch could be arranged to extend from the needle in a radial direction. As shown, the catch 206 expands to the open position upon advancement from the needle. With the catch open and accessible, the surgeon may load a suture 216 of choice into the catch outside the patient's body.

Figure 6C:
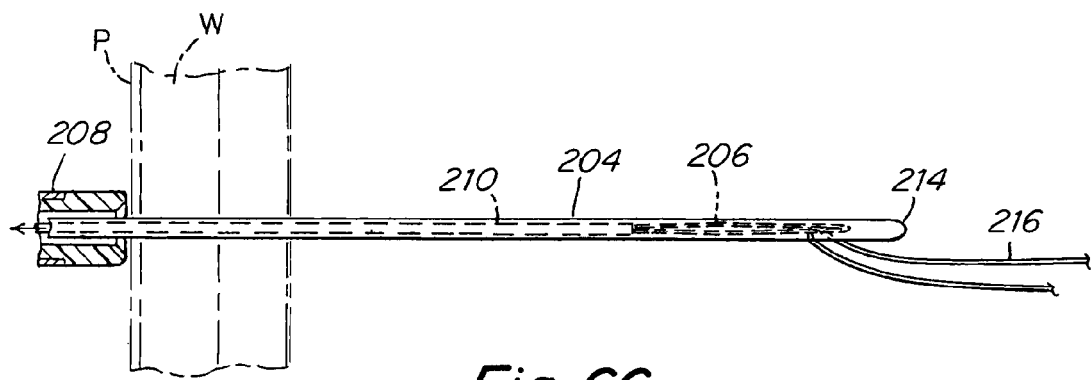
Figure 6D:
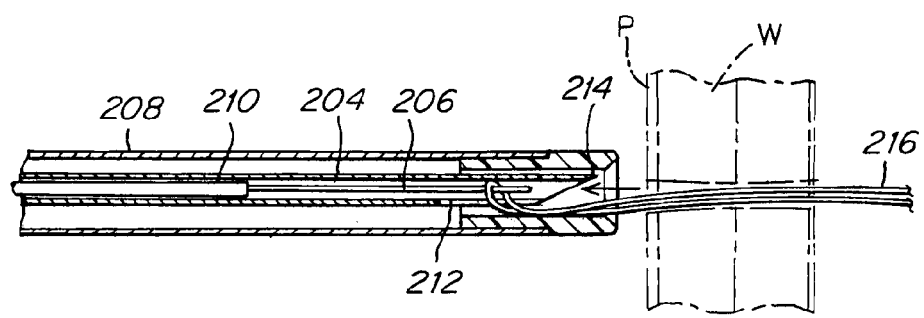

As shown in FIG. 6C, with the suture 216 loaded in the catch 206, the device may be actuated, using either the same or a different mechanism, to retract the catch into the needle 204. As shown, retraction causes the catch to collapse, thereby gripping the suture. The captured suture may then be drawn into the needle. Either simultaneously or upon further actuation, the suture passer 202 may be retracted within the shaft 208, thereby drawing the suture 216 through the abdominal wall puncture and into the shaft along with the suture passer, as shown in FIG. 6D.

With the suture captured, the distal end of the instrument 200 may be pulled into the abdominal cavity and away from the abdominal wall W, and repositioned at a second location against the wall patch P and/or fascia drawing additional suture material into the cavity. Once repositioned, the instrument may be operated, as described above, to drive the suture passer through the abdominal wall, and extend the suture catch. The extended catch may then be opened and the suture may be removed from the catch outside the body. The instrument may then be further actuated to retract the catch and the suture passer into the shaft. The suture segments may be tied off in the subcutaneous space and the incisions may be closed in a manner as should be apparent to one of skill in the art.

The above described method may be repeated to provide additional suture fixation points through the abdominal wall patch and/or fascia as desired by the surgeon for carrying out the particular repair procedure.

As indicated above, use of an instrument that can be loaded by a surgeon allows the surgeon to select and use any of various sizes and/or types of suture material when performing a transfascial suturing procedure. Additionally, such an instrument may allow a surgeon to load and deliver only as many sutures as required for a particular procedure using a single instrument, rather than possibly requiring the use of multiple preloaded instruments when the number of required sutures exceeds the capacity of the preloaded device.

An instrument 300 for delivering a transfascial suture is shown in FIGS. 7-9B. The instrument may include a pair of needles 302, or other tissue piercing elements, and a pair of suture catches 304 located within the needles that are adapted to load the needles with any suitable suture desired by the surgeon. The needles may be housed within an elongated shaft 306 and may be deployable and retractable in response to actuation of a drive mechanism included within and actuatable at a handle provided at a proximal end of the shaft. As shown, the path of the needles 302 may diverge, increasing the spacing between the needles beyond the instrument and the amount of tissue purchase thereby. In one embodiment, the shaft may include a distal tip 308 with a partition 310 configured to guide the needles in divergent directions as they are extended from the shaft. Alternatively, the needle paths may be parallel or converging.

In one embodiment, the instrument may employ suture catches similar to those described above in connection with FIGS. 2-6D. However, in contrast to the application of the suture catch for delivering a suture in and out of the abdominal cavity, the suture catches 304 may be employed to load at least the end portions of a suture into the respective needles 302 for subsequent transfascial deployment of the suture from within the abdominal cavity, through the abdominal wall to outside the abdominal cavity to secure an abdominal wall patch in position.

Each suture catch 304 is adapted to be collapsed into a closed position (FIG. 8) to grip a portion of a suture 312 and to be expanded into an open position (FIGS. 7 and 9A) to receive and/or release the suture. Each suture catch is advanceable from the distal tip of its corresponding needle 302 for receiving and/or releasing opposing ends or segments of the suture 312 and retractable into the needle for gripping and loading the needles with the suture for subsequent transfascial suturing from within the abdominal cavity. Each needle may be provided with a relief, such as a slot 314, adapted to receive a portion of the suture as it is drawn into the needle with the catch. With the suture ends loaded in the needles, the remaining length of the suture, which may include first and second suture segments, may remain outside the shaft and extend along the shaft for delivery into the abdominal cavity, although any suitable arrangement for managing the loaded suture may be employed as should be apparent to one of skill in the art.

The suture segments could be positioned externally of the needles (anywhere about the circumference of the needle including between the needles), or partially internal of the needles and partially external of the needles. For example, and without limitation, the suture segments could extend across each, respective, needle tip and then run along opposite sides of the needle bodies. Further, the suture segments may be extended partially or fully lengthwise, that is essentially or partially linearly, or may be partially or fully reduced in length such as being in the form of loops or coils. In any of such arrangements, it is preferable to load and deliver the suture segments in a fashion that minimizes tangling. The internal or external surface of the needles may be coated or otherwise finished to facilitate delivery of the suture segments without damaging the suture.

For some applications that deliver a suture from within the abdominal cavity using an inside-out procedure, a force distributing member 316 may be provided along the intermediate segment of the suture. The force distributing member may be fixed in position to the suture or may be freely moveable along a length of the suture (i.e., floating). In a fixed embodiment, the force distributing member may be joined to the intermediate segment through mechanical arrangements, such as by crimping the force distributing member to the segment or by one or more clamps or wedges provided in the force distributing member that may be engaged to the segment. Alternatively, and without limitation, the suture may be tied to the force distributing member to fix the position at the intermediate segment. Additionally, the force distributing member may be joined by thermal or chemical bonding with the suture, by heat shrinking the force distributing member to the suture, or by an adhesive applied between the two components. Further, the force distributing member may be integrally formed with the suture, such as by hardening or reshaping a portion of the suture.

The force distributing member may have any suitable configuration as should be apparent to one of skill in the art including, but not limited to, a tubular shape or a substantially plate-like or planar arrangement (including, without limitation, flat, slightly convex, slightly concave, and hybrids of the foregoing) with such substantially planar embodiments including any design suitable for spreading forces applied along the suture. An alternative arrangement is an hourglass or bow-tie configuration with openings therethrough, or along contoured edges, for passage of the suture segments. Other three-dimensional and substantially planar shapes, as well as compound shapes including three-dimensional and planar aspects, are contemplated as one of skill in the art will appreciate. Further, one or more surfaces of the force distributing member may be adapted for contact or engagement with the soft tissue repair prosthetic. For example, a tubular shaped force distributing member may include one or more specially shaped surfaces, or facets, about its circumference, which may be planar, convex, concave, or other arrangement suitable to promote contact or engagement between the force distributing member and the soft tissue repair prosthetic.

The force distributing member may be formed of a permanent material (e.g., polypropylene, polycarbonate, nylon, polyester, stainless steel, titanium), an absorbable material (e.g., polyglycolic acid (PGA), polylactic acid (PLA), polydioxanone (PDO), and blends of any of the foregoing), or a hybrid of a permanent material and an absorbable material.

Figure 8:
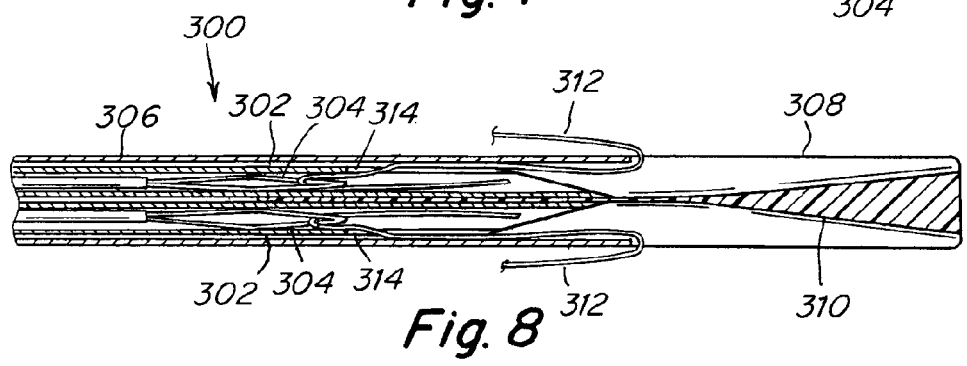
Figure 9A:
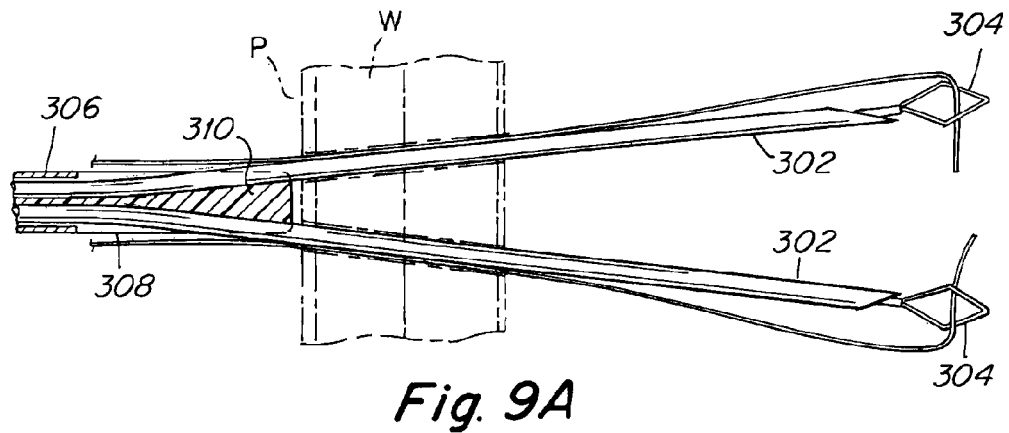

The instrument may be inserted into the abdominal cavity in a sharps-free condition with the needles 302 retracted within the shaft 306, such as shown in FIG. 8. As shown in FIG. 9A, following placement of the instrument within the abdominal cavity at a desired location against the abdominal wall patch P and/or fascia, the needles 302 may be extended at least partially from the distal end of the shaft to penetrate the abdominal wall W. In one embodiment, the needles may be extended from the shaft with a drive mechanism provided in the handle that employs a partial stroke actuation. For example, and without limitation, the drive mechanism may be adapted to extend the needles in partial strokes to incrementally penetrate the abdominal wall with each successive actuation. The drive mechanism continues to be actuated until the needles 302 either exit the skin or produce skin tenting. If desired, actuation of the device may be paused when skin tenting is observed so that the surgeon may make a skin incision prior to needle penetration, thereby lowering the force that may be necessary for the needle to penetrate the skin. Actuation of the drive mechanism continues until the needles are fully extended outside the abdominal cavity.

Figure 9B:
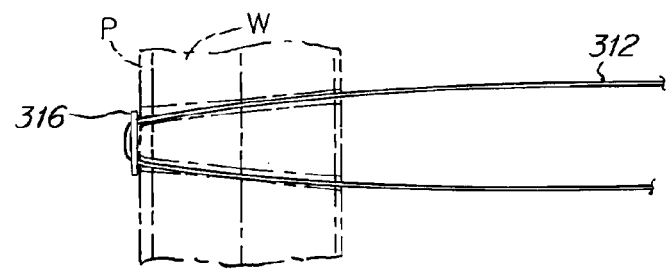

As shown in FIG. 9A, further actuation of the device, which may involve engagement of the same or a different mechanism, extends the suture catches 304 from the distal tip of each needle. As shown, each catch expands to the open position upon advancement from the needle. With the catches open and accessible, the surgeon may remove the suture ends. Further actuation of the device, using either the same or a different mechanism, retracts each catch into its respective needle. Either simultaneously or upon further actuation, the needles are withdrawn from the abdominal wall and retracted into the shaft with a U-shaped suture being transfascially delivered through the abdominal wall, as shown in FIG. 9B.

After both suture segments are fully deployed out of the instrument, whether by advancement of the needles or by pulling of the suture tails or tail segments that have been transfascially delivered, the force distributing member, if desired, and intermediate segment will position against the soft tissue repair patch. The suture segments may be tied off in the subcutaneous space and the incisions may be closed in a manner as should be apparent to one of skill in the art.

The instrument may be reloaded and used to provide additional suture fixation points through the abdominal wall patch and/or fascia as desired by the surgeon for carrying out the particular repair procedure.

Figure 7:
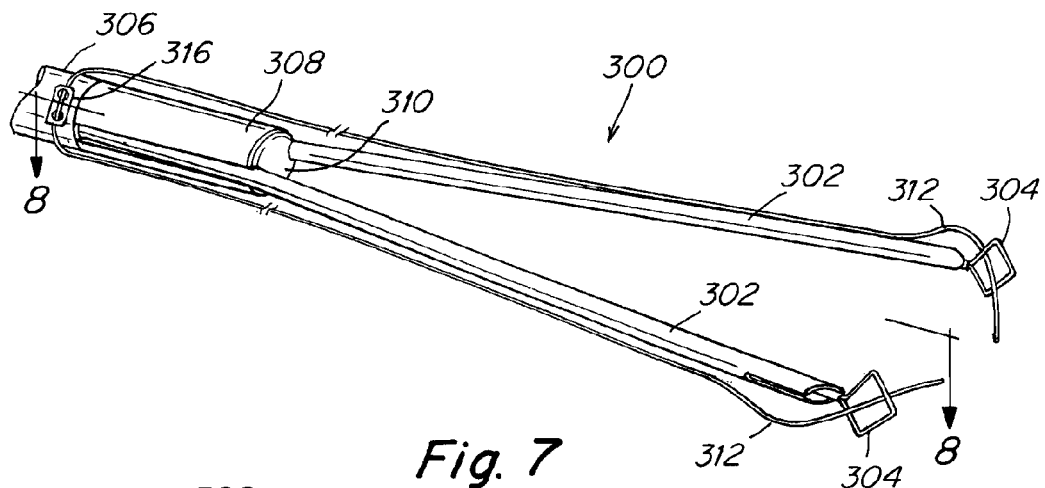
FIGS. 7-9B are illustrations of an instrument for transfascial delivery of a suture with a pair of suture catches that are loadable with a suture.

A system for actuating one or more needles or other tissue piercing elements of a delivery instrument, such as the instrument 300 illustrated in FIGS. 7-8, is shown in FIGS. 10-16. The actuating system 400 includes a handle body 402 which supports a needle drive mechanism adapted to actuate one or more needles or other tissue piercing elements in one or more partial strokes. The actuating system 400 may also include a suture catch drive mechanism that is supported by the handle body 402 and is adapted to actuate one or more suture catches.

Figure 10:
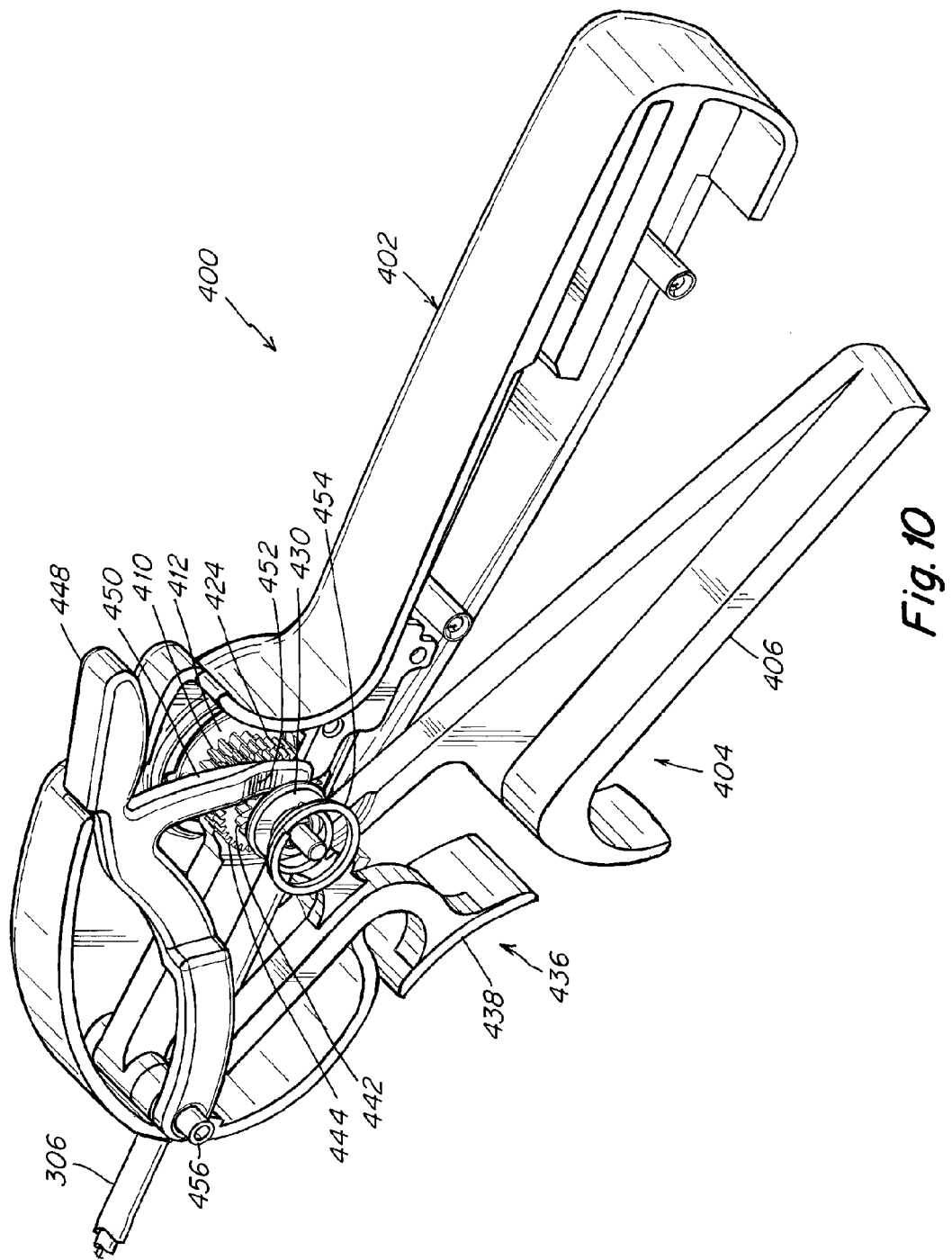
Figure 11:
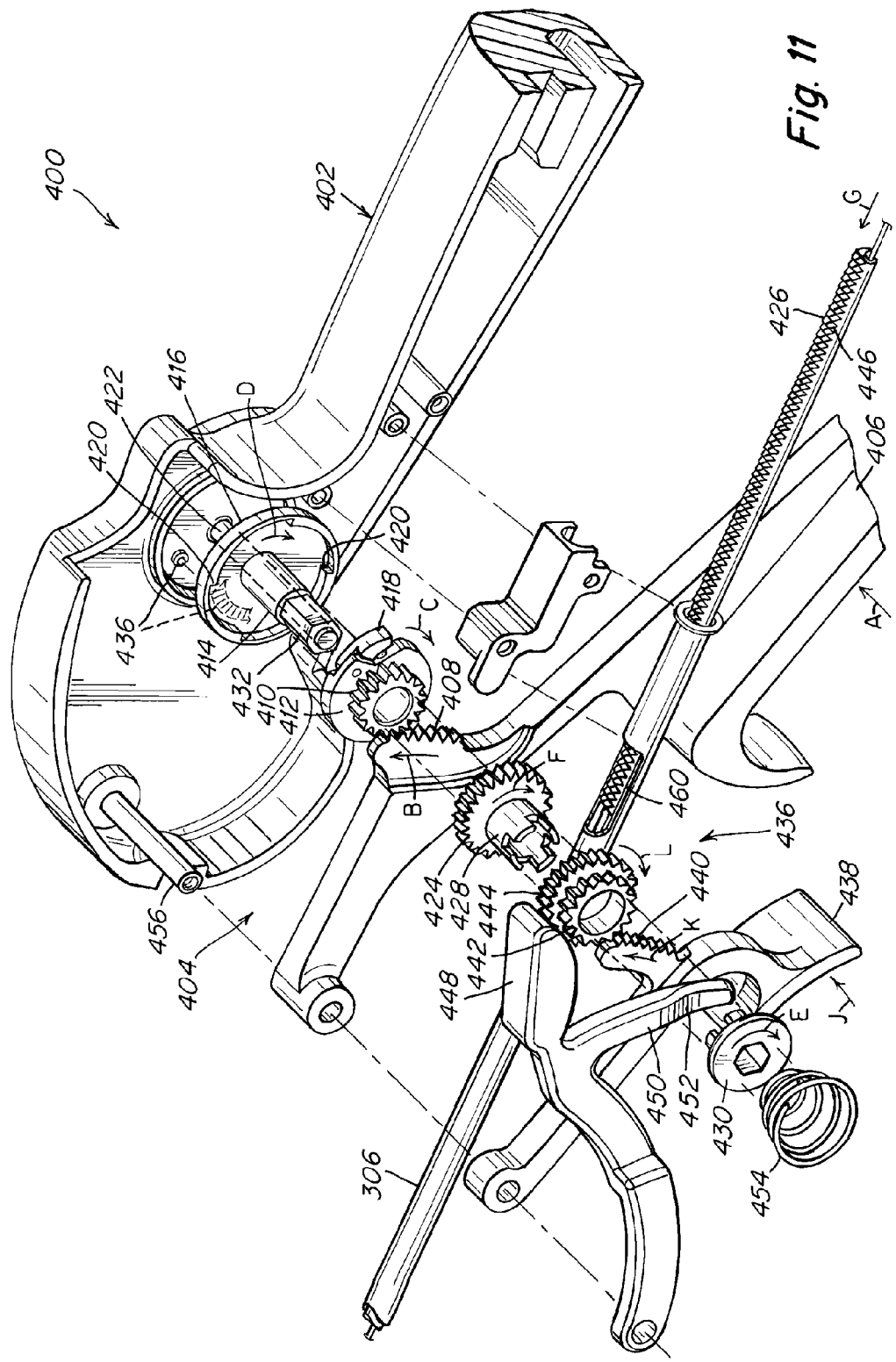

As shown in FIGS. 10-11, the needle drive mechanism 404 may include a needle actuating lever 406 with a rack 408 that operatively engages a drive aspect 410 of a clutch input gear 412 to rotate the clutch input gear in response to movement of the lever. The clutch input gear 412 may be rotatably supported on an output shaft 414 of a clutch output gear 416 and may include one or more features, such as pawls 418, that operatively engage with corresponding features, such as detents 420, provided on the clutch output gear. Rotation of the clutch input gear 412 (arrow C) in response to movement of the needle actuating lever 406 (arrow A), and consequently the lever rack 408 (arrow B), rotates the clutch output gear 416 (arrow D) and consequently the output shaft 414 about a fixed axle 422.

A needle drive pinion gear 424 may be rotatably supported on the output shaft 414 adjacent the clutch input gear 412 and in operative engagement with a needle rack 426 that is coupled to one or more needles or other tissue piercing elements. The needle drive pinion gear 424 may be coupled to the output shaft 414 with a split hub arrangement. As shown, a needle drive split hub 428 of the needle drive pinion may operatively engage a rack release split hub 430 that is keyed to a hex drive 432 of the output shaft. Rotation of the output shaft 414 rotates the rack release split hub 430 (arrow E) which in turn rotates the needle drive slit hub 428 of the needle drive pinion gear, when engaged, and consequently the needle drive pinion gear 424 (arrow F). Rotation of the needle drive pinion gear 424 drives the needle rack 426 (arrow G) to advance the one or more needles or other tissue piercing elements along and from the elongated shaft 306 of the instrument.

A pawl and detent arrangement between the clutch input and output gears 412, 416 permits the clutch input gear to rotate in the opposite direction relative to the clutch output gear upon release of the needle actuating lever. A ratchet arrangement 436 may be provided to allow the clutch output gear 416 to rotate only in one direction (e.g., clockwise as illustrated by arrow D in FIG. 11). Such an arrangement allows the clutch input gear 412 to reset relative to the clutch output gear 416 upon release of the needle actuating lever 406 to permit multiple actuations of the lever for advancing each needle in one or more partial strokes. In this manner, preventing the clutch output gear 416 from rotating as the clutch input 412 gear resets upon release of the needle actuating lever 406 prevents the needle drive pinion gear 424 from rotating, thereby holding the needle rack 426, and consequently each needle, in its advanced position.

As shown in FIG. 11, the suture catch drive mechanism 436 may include a catch actuating lever 438 with a rack 440 for operatively engaging a drive aspect 442 of a catch drive pinion gear 444 to rotate the catch drive pinion gear in response to movement of the lever. The catch drive pinion gear 444 may be rotatably supported on the needle drive split hub 428 adjacent the needle drive pinion gear 424. The catch drive pinion gear 444 is in operative engagement with a catch rack 446 that is coupled to one or more suture catches. Rotation of the catch drive pinion gear 444 (arrow L) in response to movement of the catch actuating lever 438 (arrow J), and consequently the lever rack 440 (arrow K), drives the catch rack 446 to advance the one or more suture catches from the distal end of each needle.

The catch drive mechanism may be arranged so that the lever rack 440 does not engage the drive aspect 442 of the catch drive pinion gear 444 until the catch drive actuating lever 438 is actuated. This arrangement permits the catch drive pinion gear to rotate as the needles are being extended and/or retracted via the needle rack.

Releasing the catch actuating lever 438 allows the catch rack 446, and consequently the suture catches, to retract to their respective initial or non-actuated positions. This may be accomplished by biasing the catch rack and/or the catch actuating lever toward their respective initial or non-actuated positions. A spring, such as a torsion or compression spring, may be employed to bias the catch actuating lever and/or catch rack to the initial or start position. However, other arrangements may be employed to retract each suture catch as should be apparent to one of skill in the art.

As illustrated, the needle rack 426 and the catch rack 446 may be positioned side-by-side in a split rack arrangement where each rack may move separately in a longitudinal direction. However, other arrangements are contemplated for advancing the needles and catches as should be apparent to one of skill in the art.

Each needle may be retracted by actuating a release lever 448 to drive the rack release split hub 430 out of engagement with the needle drive split hub 428. As shown in FIGS. 10-11, the release lever 448 may include a release arm 450 that is adapted to engage and release the rack release split hub 430 upon actuation of the release lever. The release arm 450 may include a cam surface 452 that is configured to engage and drive the rack release split hub in an axial direction away from the needle drive split hub 428 as the release lever 448 is pressed in a downward direction. The rack release split hub 430 may be biased into engagement with the needle drive split hub 428 using a spring 454, such as a compression spring.

Once disengaged from the rack release split hub 430, the needle drive pinion gear 424 is free to rotate about the output shaft 414 to allow the needle rack 426, and consequently each needle, to retract into the outer shaft 306 of the instrument. The needle rack 426 may be biased toward its retracted position using a spring, such as a compression spring (not shown), as should be apparent to one of skill in the art.

As shown in FIGS. 10-11, the needle actuating lever 406, the catch actuating lever 438 and the release lever 448 may be pivotally mounted to a fixed axle 456. Each lever may be biased toward its initial or non-actuated position, such as with a spring (not shown), so that each lever will return to its respective non-actuated position when released by the user following actuation of the lever.

Figure 12:
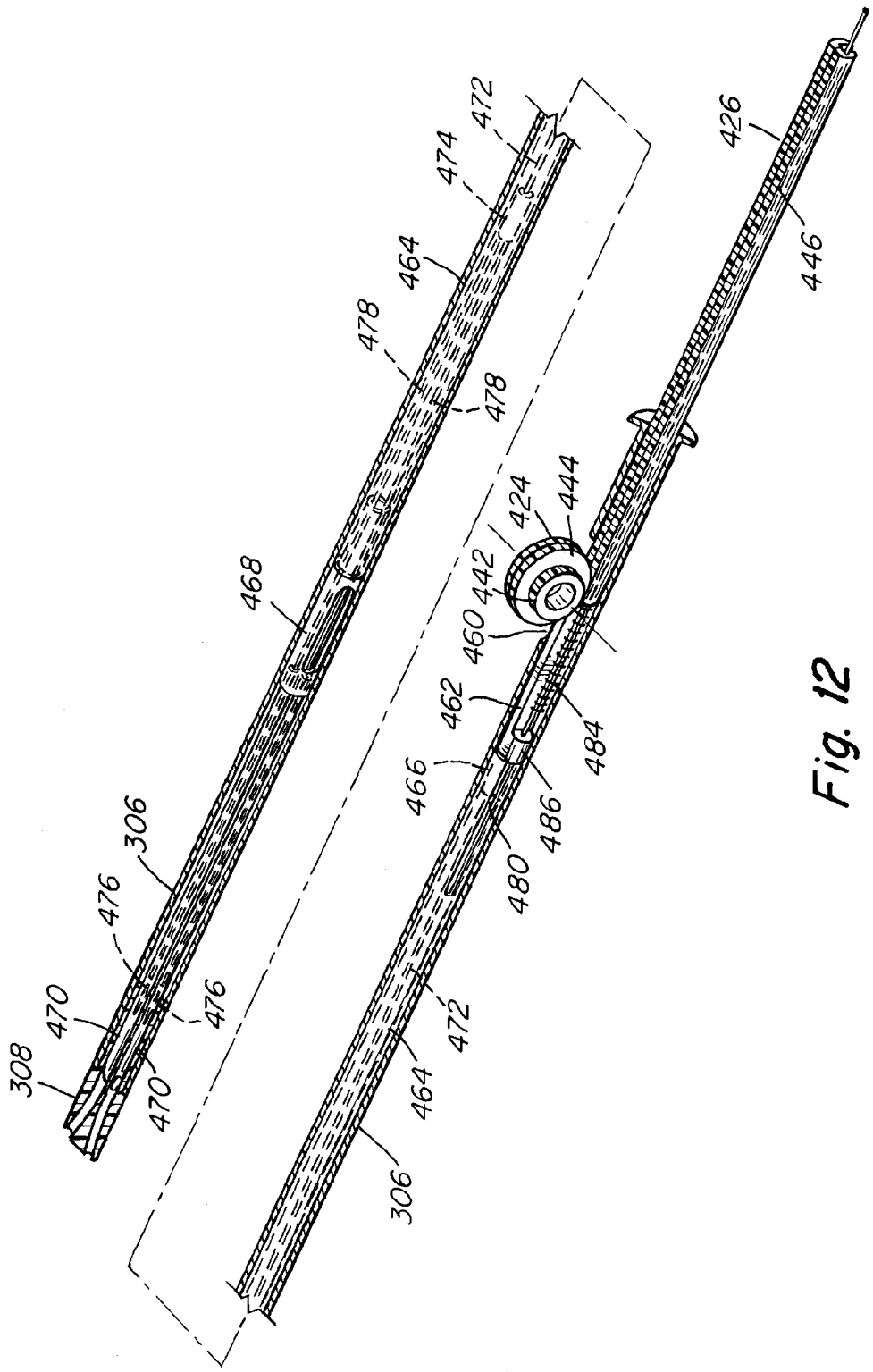

As shown in FIGS. 12-14, the needle rack 426 and the catch rack 446 extend through a proximal end of the outer shaft 306 and along a portion of the shaft. The outer shaft has an opening 460 for the needle drive pinion gear 424 and the catch drive pinion gear 444 to engage the needle and catch racks, respectively.

As shown in FIGS. 12-14, the needle rack 426 includes an extension 462 configured to extend beyond the distal end of the catch rack 446 and conform closely to the outer shaft for stabilizing the needle and catch racks as they are moved along the shaft. A needle drive tube 464 may be coupled to a reduced neck 466 at the distal end of the needle rack extension 462. A needle coupler 468 may be located at the distal end of the needle drive tube 464 with one or more needles 470, preferably hollow needles, coupled to and extending from the needle coupler. As shown in FIG. 13, when actuated by the needle actuating lever, the needle drive pinion gear 424 rotates (arrow F) to drive the needle rack 426 in a distal direction (arrow G) along the outer shaft to extend each needle 470 from the distal end of the shaft via the needle drive tube 464.

A catch drive wire or tube 472 may be coupled to the distal end of the catch rack 446 with a catch coupler 474 located at the distal end of the catch drive 472. One or more suture catches 476 may be coupled to and extend from the catch coupler 474 via one or more drive wires, such as hypotubes 478. As shown, the catch drive wire 472 may extend through the needle rack extension 462 and along the needle drive tube 464. The hypotubes 478 may extend from the catch coupler 474, which is located within the needle drive tube 472, through the needle coupler 468 and into each needle 470 to position a suture catch within each needle.

As shown in FIGS. 14 and 16, the catch drive wire 472 may include an offset portion 480 that operatively engages a corresponding groove 482 (shown in fragmented view of FIG. 16) or other feature on the needle rack extension 462. With this arrangement, distal movement of the needle rack 426 engages and simultaneously advances the catch drive wire 472, and consequently the catch rack 446 and suture catches 476, in the distal direction (arrow H). In this manner, each suture catch 476 maintains its relative position within the needle 470 as the needle is advanced along and extended from the shaft as shown in FIG. 13 (arrow I).

As shown in FIGS. 15-16, when actuated by the catch actuating lever 438, the catch drive pinion 444 gear rotates (arrow L) to drive the catch rack 446 in a distal direction (arrow M) independent of the needle rack 426 and along the outer shaft. Distal movement of the catch rack 446 advances the catch coupler 474 (arrow N), and consequently the catch hypotubes 478, through the needle drive tube 472 to extend each catch 476 from the distal end of a needle 470. When extended from the needle, as shown in FIG. 15, each suture catch 476 may open (arrow O) for loading or releasing a suture.

As shown in FIG. 16, advancement of the catch rack 446 disengages the offset portion 480 of the catch drive from the needle rack extension 462. A spring 484, such as a compression spring, may be located between the distal end of the catch rack 446 and the proximal end of a shoulder 486 of the needle catch extension 462 for biasing the catch rack in the proximal direction. As shown, the spring 484 may be positioned about and along a portion of the catch drive wire 472. When the catch rack 446 is advanced to extend the suture catches 476, the spring 484 is compressed between the catch rack and the needle rack extension to generate a force sufficient to return the catch rack 446 to its initial or non-actuated position relative to the needle rack 426 to thereby retract each catch 476 into a needle 470 when the catch lever 438 is released by a user. When loaded with suture, retraction of each needle 470 will collapse each suture catch 476 to thereby grip and draw a suture segment into the needle.

Actuation of the needle actuating lever 406 will advance the needle rack 426, and consequently each needle 470, a predetermined distance along the shaft of the instrument. The needle drive mechanism may be configured to incrementally extend each needle to a fully extended position with two or more partial strokes in response to two or more lever actuations.

In one embodiment, the needle drive mechanism may be configured to extend each needle 470 approximately 0.2 inches beyond the distal end of the shaft in response to the first or initial actuation of the needle actuating lever 406. Thereafter, each subsequent actuation of the needle actuating lever 406 may further extend each needle an additional 1.0 inches from the shaft. The needle drive mechanism may be configured to fully extend each needle 470 with two to five actuations of the needle actuating lever. However, the needle drive mechanism may be configured to extend each needle using any size and/or number of increments as should be apparent to one of skill in the art.

As indicated above, it may be desirable for some applications to employ an instrument for delivering a transfascial suture that is operated to control advancement and/or penetration of the tissue piercing element or needle through the abdominal wall. The instrument may be configured to advance the drive member or needle in partial strokes, rather than a single full stroke, with each actuation of the device. If desired, actuation of the device may be paused when skin tenting is observed so that the surgeon may make a skin incision prior to needle penetration, thereby lowering the force that may be necessary for the needle to penetrate the skin. For some applications, it may be desirable to identify needle location during deployment, such as by skin tenting or palpation, and/or to penetrate the abdominal wall in a manner that reduces potential contact with the sharpened tip of the needle as it penetrates through the skin.

An instrument 500 for delivering a transfascial suture is shown in FIGS. 17A-17D and may include a needle 502, or other tissue piercing element, and a tissue probe 504 located within the needle. The needle 502 may be housed within an elongated shaft 506 and may be operated with a drive mechanism included within and actuatable at a handle provided at a proximal end of the shaft.

The probe 504 is advanceable from the needle 502 to extend beyond the needle tip to facilitate identifying the location of the needle via skin tenting and/or palpation by the surgeon. The probe may be configured with a blunt distal end which provides sharps protection as the needle is advanceable through portions of the abdominal wall and/or skin. The probe may be formed of any suitable material including, but not limited to, metal and plastic having sufficient rigidity for penetrating through less dense regions of the abdominal wall, including fat and the dermal layer.

Figure 17A:
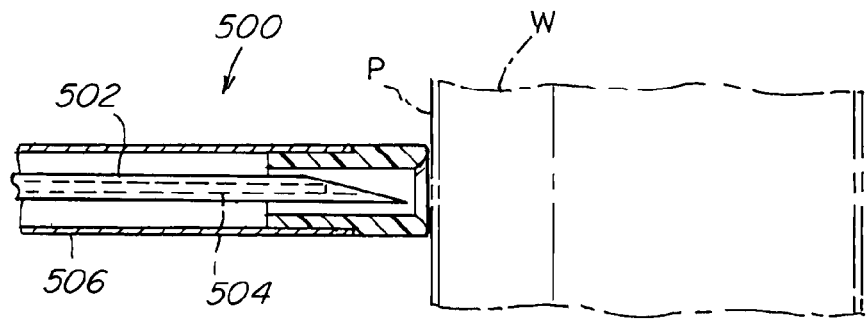
FIGS. 17A-17D are illustrations of an instrument for transfascial delivery of a suture with a tissue probe.
Figure 17B:
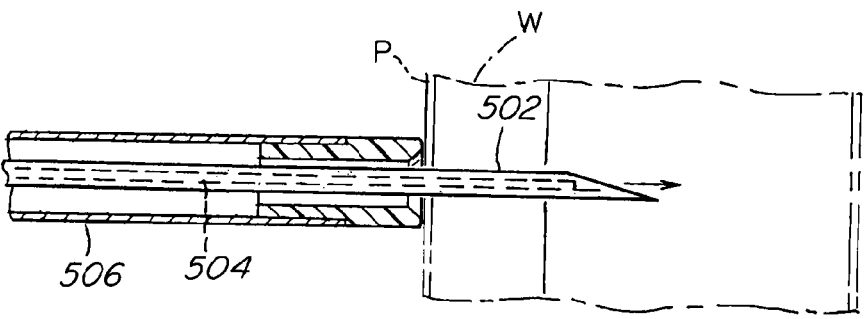

In one embodiment shown in FIGS. 17A-17B, the instrument may be inserted into the abdominal cavity in a sharps-free condition with the needle 502 retracted within the shaft 506. Following placement of the instrument against the abdominal wall patch and/or fascia, the instrument may be actuated to present a portion of the needle 502 beyond the shaft 506 sufficient to penetrate the most dense tissue of the abdominal wall. The needle may be partially extended from the distal end of the shaft or the shaft may be partially retracted to expose the needle tip. Thereafter, the probe 504 may be extended from the needle and advanced, either alone or together with the needle, through less dense tissue and/or fat toward the surface of the skin. The instrument may employ any suitable drive mechanism to accomplish the desired action as should be apparent to one of skill in the art.

Figure 17C:
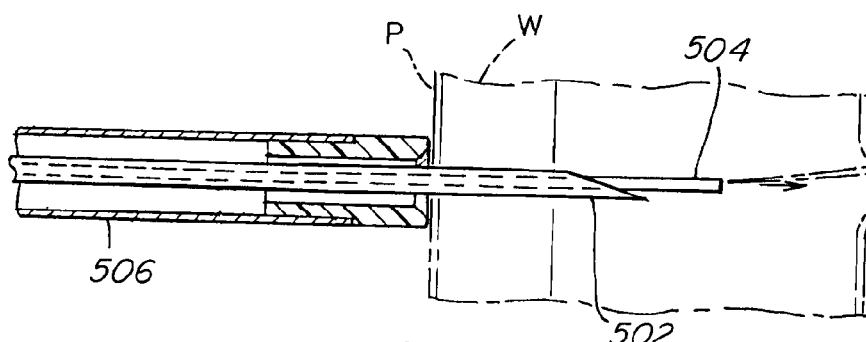
Figure 17D:
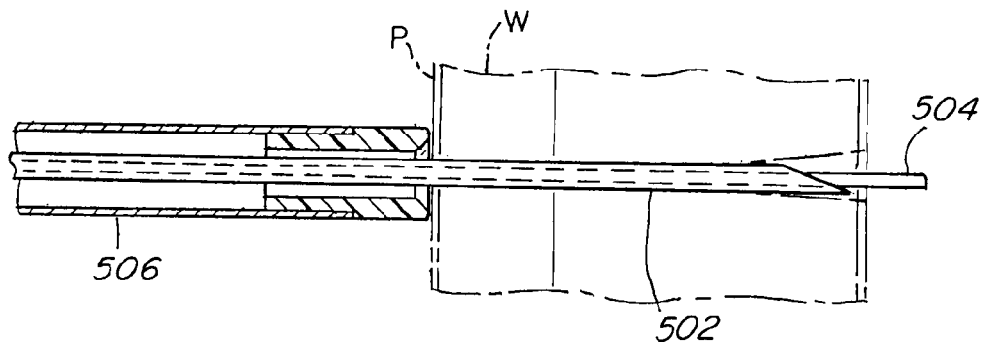

As shown in FIGS. 17C-17D, after deployment of the probe 504, the needle 502 may be further advanced with one or more partial strokes, until the probe either exits the skin or produces skin tenting. If desired, actuation of the device may be paused when skin tenting is observed so that the surgeon may make a skin incision prior to penetration of the probe, thereby lowering the force that may be necessary for the needle to penetrate the skin. Actuation of the drive mechanism continues until the needle 502 and the probe 504 are fully extended through the abdominal wall.

The tissue probe arrangement may be integrated with any one or more of the transfascial suturing instruments described above. In one embodiment, the instrument 500 may include a suture catch, similar to that described in connection with FIGS. 2-9A, that is located within and advanceable along a hollow probe. Other applications of a tissue probe arrangement are contemplated as should be apparent to one of skill in the art.

An instrument 600 for delivering a transfascial suture using either an inside-out technique or an outside-in technique is shown in FIGS. 18A-18D. The instrument may be used within the abdominal cavity to pass a suture in either direction through the abdominal wall. The instrument may include a suture passer 602 for passing a suture through the abdominal wall at a first location, either into the abdominal cavity from outside a patient's body or from inside the abdominal cavity to outside the body, and passing the suture through the abdominal wall at a second location, either from inside the abdominal cavity to outside the body or into the abdominal cavity from outside the body.

The suture passer may include a needle 604, or other tissue piercing element, and a suture catch 606 located within the needle. The suture passer 602 may be housed within an elongated shaft 608 and may be operated with a needle drive mechanism included within and actuatable at a handle 610 provided at a proximal end of the shaft. The suture catch may be located within the needle and operated with a catch drive mechanism that is also included within and actuatable at the handle. The needle and catch may be actuated with the same or different drive mechanisms.

In one embodiment, the suture passer 602 may be similar to the passer of FIGS. 2-5 described above, although other suture passers are contemplated for use with the instrument.

In one embodiment, the shaft 608 is retractable in a proximal direction to expose the distal end or tip of the needle 604. As shown, the needle may extend through and be connected to the handle to fix the needle in position relative to the handle. The shaft 608 may be biased in the distal direction to enclose the needle tip for sharp-free insertion and manipulation within the abdominal cavity. As shown, a spring 612, such as a compression spring, may be located about a proximal portion of the needle and coupled to the proximal end of the shaft with a coupler 614 that is movable along the proximal portion of the needle. With the distal end of the shaft placed against a patch P and/or the abdominal wall W, pushing the handle 610 forward in the distal direction causes the shaft 608 to retract proximally into the handle as the needle 604 is driven into the wall.

To control retraction of the shaft, for example, to reduce the potential of inadvertent retraction of the shaft that may lead to premature exposure of the needle tip, the instrument may include a shaft locking mechanism that secures the shaft in one or more positions, including the distally extended position over the needle tip. In one embodiment, the locking mechanism may include a lock 616 movably supported in the handle to engage and secure the shaft in one or more positions, including the extended position. As shown in FIG. 18A, the lock 616 may include a projection 618 that engages a corresponding feature, such as a notch 620, at a proximal end of the shaft to lock the shaft in the extended position. The lock may be coupled to a release trigger 622 adapted to disengage the lock from the notch to allow the shaft to be retracted into the handle along the needle. The trigger may be biased with a spring 624, such as a compression spring, to urge the lock into a locked position for engagement with the shaft. It is to be appreciated that other suitable lock arrangements may be employed as should be apparent to one of skill in the art.

As shown in FIG. 18B, the shaft 608 may include at least one additional feature, such as a distal notch 626, that engages with the lock when the shaft has been retracted a predetermined distance into the handle, which may correspond to a fully retracted position, to expose the needle. Such an arrangement may be advantageous to maintain the shaft in a retracted position without requiring a user to maintain a forward distal force against the abdominal wall. Additional features, such as additional notches, may be provided along the shaft between the proximal and distal notches 620, 626 to control the amount of shaft retraction and needle extension beyond the distal end of the shaft. Such features may be desirable to permit incremental penetration of the needle into and through the abdominal wall, rather than driving the needle through the entire wall with a single full stroke.

The instrument may also include a catch drive mechanism for operating the suture catch. In one embodiment, the catch drive mechanism may include a trigger 628 that is coupled to the proximal end of a drive member 630, such as a wire, for the suture catch. The trigger may be pivotally supported on the handle such that actuation of the trigger in a forward or distal direction advances the drive wire 630 along the needle to extend the suture catch 606 from the distal end of the needle, as shown in FIG. 18B. Movement of the catch trigger 628 in the opposite direction draws the drive wire along the needle in the proximal direction to retract the catch into the needle. If desired, the catch trigger may be biased to a non-actuated position with a spring, such as a torsional or compression spring, to maintain and/or retract the catch within the needle upon release or absent a positive actuation of the trigger by a user to extend and then hold the catch in the extended, deployed position.

An illustrative method of delivering a transfascial suture using the instrument 600 will be described in connection with FIGS. 18A-18D.

The instrument may be inserted into the abdominal cavity in a sharps-free condition with the needle 604 housed within the shaft 608. As shown in FIG. 18A, following placement of the instrument within the abdominal cavity at a desired location against the abdominal wall patch P and/or fascia, the shaft 608 may be unlocked by actuating the release trigger 622 which disengages the lock 616 from the shaft.

As shown in FIG. 18B, with the shaft unlocked, the instrument may be pushed in the distal direction against the abdominal wall patch and/or fascia causing the shaft 608 to retract into the handle 610 against the force of the spring 612 as the needle 604 is driven through the abdominal wall W and skin. When the shaft becomes fully retracted, the lock 616 engages a distal notch 626 in the shaft to lock the shaft in the retracted position and prevent further advancement of the needle through the abdominal wall. If desired, the lock may engage one or more intermediate notches to incrementally limit retraction of the shaft and thereby control penetration of the needle through the abdominal wall in one or more partial strokes.

As shown in FIG. 18B, with the needle 604 fully deployed through the abdominal wall, the suture catch 606 may be deployed from the needle by actuating the catch trigger 628. As shown, the catch expands to the open position upon advancement from the needle. With the catch deployed and open, the surgeon may load a suture 628 of choice into the catch outside the patient's body.

As shown in FIG. 18C, with the suture 628 loaded in the catch 606, the catch trigger 628 may be released to assume its initial or non-actuated position to retract the catch into the needle 604. Retraction causes the catch to collapse, thereby gripping the suture and drawing the suture into the needle.

As shown in FIG. 18D, with the suture captured, the release trigger 622 may be actuated to disengage the lock 616 from the shaft as the instrument 600 is pulled into the abdominal cavity and away from the abdominal wall, thereby allowing the shaft to extend from the handle 610 and along the needle, due to the biasing force of the spring 612, to its fully extended position to cover the needle tip. Once the shaft is fully extended, the lock 616 reengages the proximal notch 620 to lock the shaft in the extended position over the needle.

The instrument may be repositioned at a second location against the wall patch and/or fascia drawing additional suture material into the abdominal cavity. Once repositioned, the instrument may be operated, as described above, to drive the needle through the abdominal wall, and extend the suture catch. With the catch extended and open, the suture may be removed from the catch outside the body. The catch may then be retracted and the shaft extended over the needle. The suture segments may be tied off in the subcutaneous space and the incisions may be closed in a manner as should be apparent to one of skill in the art.

The above described method may be repeated to provide additional suture fixation points through the abdominal wall patch and/or fascia as desired by the surgeon for carrying out the particular repair procedure.

Figure 19:
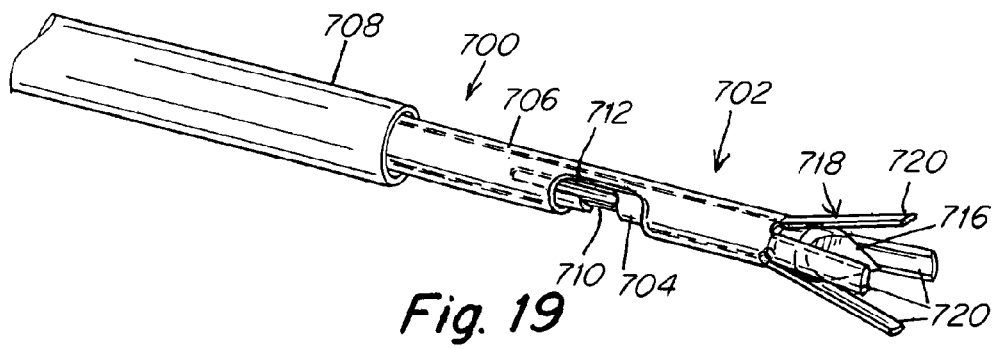
FIGS. 19-19F are illustrations of an instrument for transfascial delivery of a suture with a suture catch.
Figure 19A:
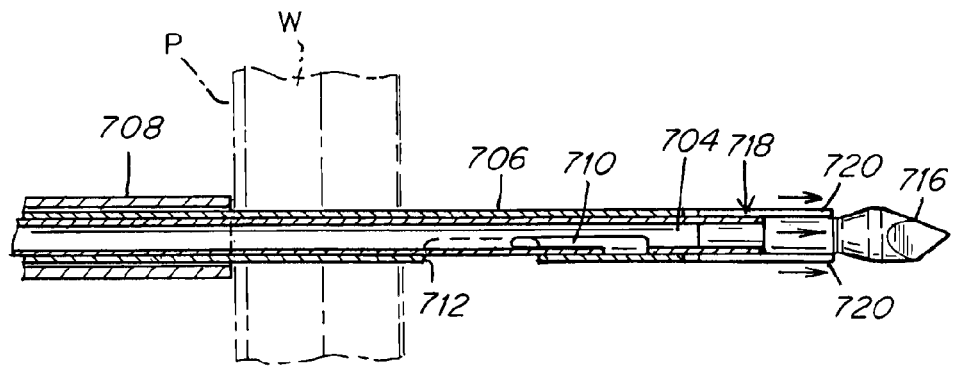
Figure 19B:
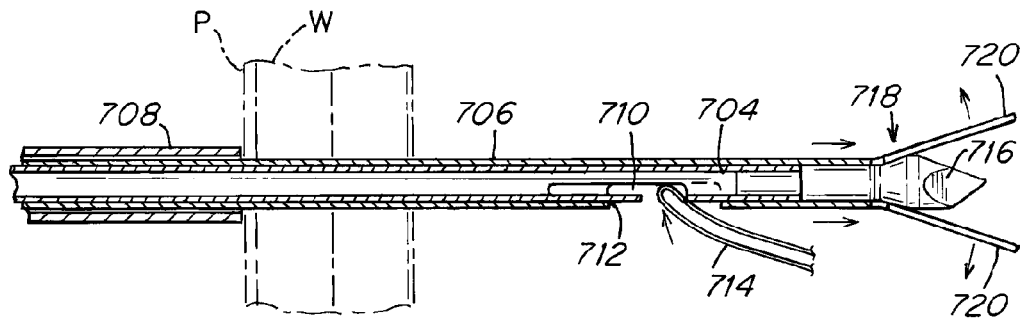
Figure 19C:
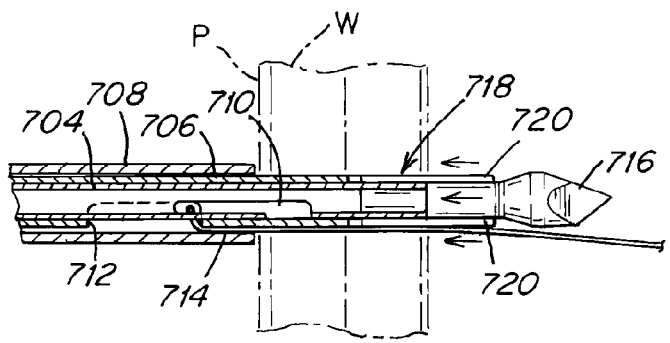
Figure 19D:
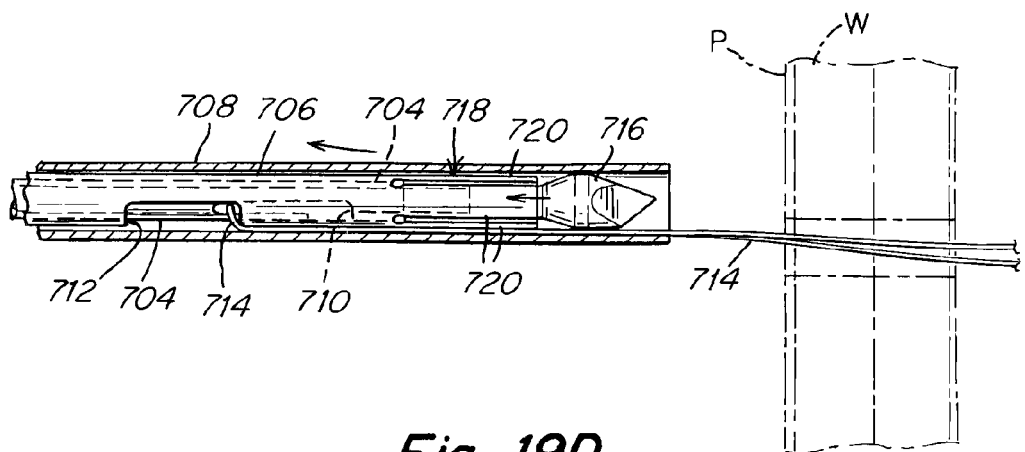
Figure 19E:
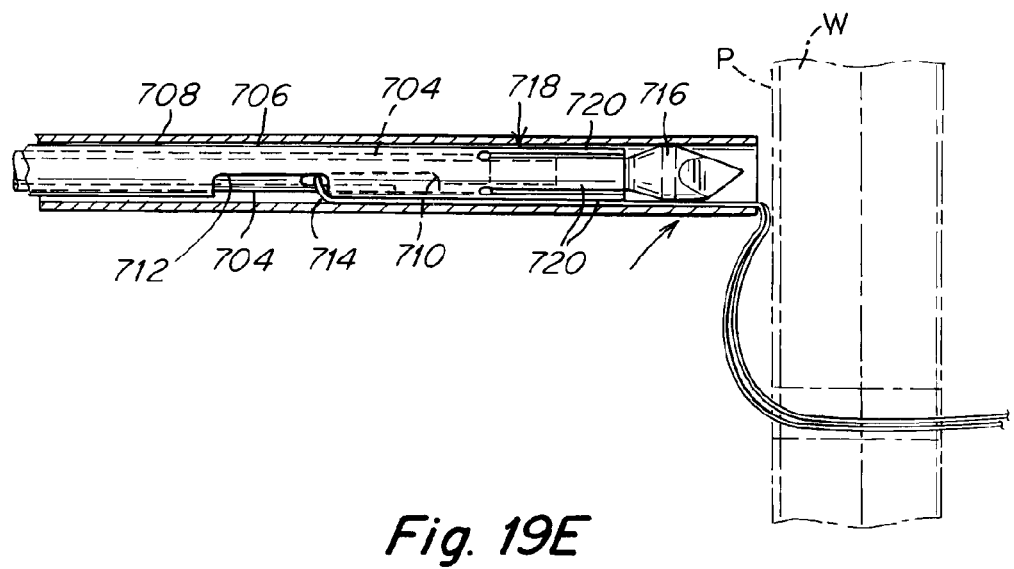
Figure 19F:
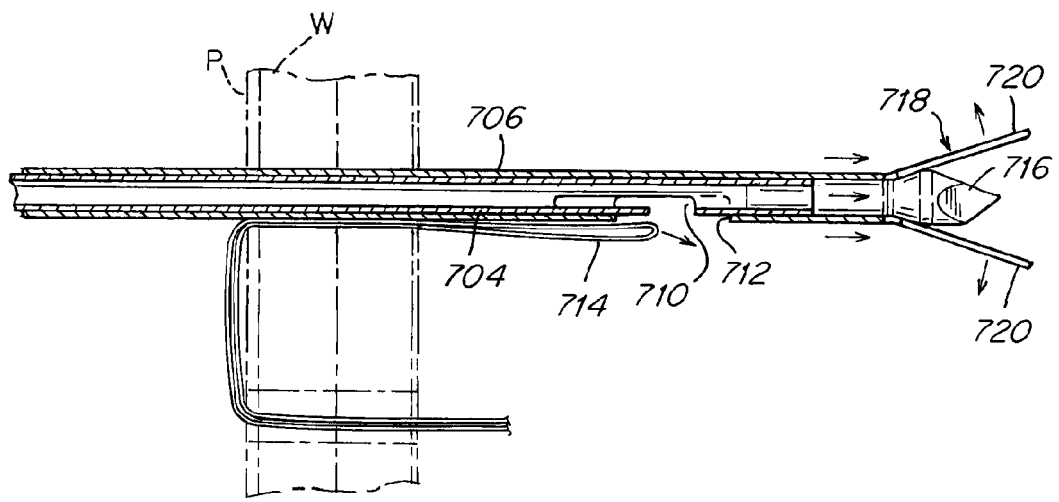

An instrument 700 for delivering a transfascial suture is shown in FIGS. 19-19F and may include a suture passer 702 for drawing a suture at a first location into the abdominal cavity from outside a patient's body and passing the suture at a second location from inside the abdominal cavity to outside the body. The suture passer may include a needle 704, or other tissue piercing element, and an outer sleeve 706 extending along at least a portion of the outer surface of the needle. The suture passer 702 may be housed within an elongated shaft 708 and may be operated with a drive mechanism included within and actuatable at a handle provided at a proximal end of the shaft.

As shown in FIGS. 19-19B, the needle 704 may include a suture catch 710 adapted to receive a portion of a suture to pass the suture in and out of the abdominal cavity. The outer sleeve 706 is movable relative to the needle 704 and may include an opening 712 that may be positioned over the catch 710 so that a suture 714 may be received within and released from the catch. The suture may be captured by repositioning the opening 712 relative to the catch 710 so that a portion of the sleeve 706 overlies and blocks the catch.

In one embodiment, the sleeve may be longitudinally slidable along the needle between a closed position in which the opening is spaced in a proximal direction away from the catch (FIG. 19A) and an open position in which the opening overlies and exposes the catch (FIG. 19B). Alternatively, and without limitation, the needle may be longitudinally slidable within the sleeve to cover and expose the catch. As another alternative, and without limitation, the sleeve or needle may be rotated and/or slidable between open and closed positions.

As shown, the catch 710 may be spaced in a proximal direction away from the needle tip 716 to reduce potential contact with the tip as a suture is captured with and released from the catch. If desired, the suture passer may include a shield to further isolate the needle tip as a suture is loaded into and unloaded from the catch. In one embodiment as shown in FIGS. 19 and 19B, a needle shield 718 may be provided at the distal end of the outer sleeve 706 to cover and guard the needle tip 716 when the sleeve is positioned to expose the catch. The shield may include a plurality of shield segments 720 that extend over and isolate the needle tip by moving the sleeve and/or needle to open the catch.

As shown in FIG. 19A, the shield segments may be adapted to lie against the needle and proximal to the needle tip when the sleeve is positioned to close the catch. As shown in FIG. 19B, the shield segments may be adapted to coact with a proximal tapered surface of the needle tip and flare outwardly as the opening in the outer sleeve is positioned over the catch. In one embodiment, the shield segments may be resilient and biased inwardly toward the needle so that the shield 718 presses against the needle tip 716 when the outer sleeve is extended (FIG. 19B) to expose the catch and the shield returns to its position against the needle body (FIG. 19A) when the outer sleeve is retracted to close the catch.

An illustrative method of delivering a transfascial suture using the instrument 700 of FIG. 19 will be described in connection with FIGS. 19A-19F.

The instrument may be inserted into the abdominal cavity in a sharps-free condition with the suture passer 702 retracted within the shaft 708. As shown in FIG. 19A, following placement of the instrument within the abdominal cavity at a desired location adjacent or against the abdominal wall patch P and/or fascia, the suture passer 702 may be extended from the distal end of the shaft with the needle tip exposed to penetrate the abdominal wall W and skin. In one embodiment, the suture passer may be extended from the shaft with a drive mechanism provided in the handle that employs a multi-stage and/or partial stroke actuation. For example, and without limitation, the drive mechanism may be adapted to extend the suture passer in partial strokes to incrementally penetrate the abdominal wall with each successive actuation. The drive mechanism continues to be actuated until the needle either exits the skin or produces skin tenting. If desired, actuation of the device may be paused, either when skin tenting is observed or to otherwise locate the needle via palpation of the abdominal wall, so that the surgeon may make a skin incision prior to needle penetration, thereby lowering the force that may be necessary for the needle to penetrate the skin. Actuation of the drive mechanism continues until the suture passer is fully extended to present the suture catch outside the abdominal cavity.

As shown in FIG. 19B, further actuation of the device, which may involve engagement of the same or different mechanism, extends the outer sleeve in a distal direction to open the catch by positioning the opening over the catch. The shield is also extended over the needle tip to isolate the tip from potential contact therewith outside the abdominal cavity with the needle extending through the wall W. With the catch accessible and the needle tip shielded, the surgeon may load a suture into the catch outside the patient's body.

As shown in FIG. 19C, with the suture 714 loaded in the catch 710, the device may be actuated, using either the same or a different mechanism, to retract the outer sleeve 706 along the needle to cover and close the catch. Either simultaneously or upon further actuation, the suture passer is retracted into the shaft, thereby drawing the suture through the abdominal wall puncture and into the shaft along with the suture passer.

As shown in FIGS. 19D-19F, the instrument may be pulled into the abdominal cavity and away from the abdominal wall W, and then repositioned at a second location adjacent or against the wall patch P and/or fascia drawing additional suture material into the cavity. Once repositioned, the instrument may be reactuated, as described above, to drive the suture passer through the abdominal wall with the suture, expose the suture catch and shield the needle tip. With the catch exposed, the suture may be removed from the catch outside the body. The instrument may then be actuated to retract the suture passer into the shaft. The suture segments may be tied off in the subcutaneous space and the incisions may be closed in a manner as should be apparent to one of skill in the art.

The above described method may be repeated to provide additional suture fixation points through the abdominal wall patch and/or fascia as desired by the surgeon for carrying out the particular repair procedure.

An instrument 800 for delivering a transfascial suture is shown in FIGS. 20-23C and may include a suture passer 802 with a pair of suture guide elements 804, which may be in the form of needles, extending from a distal end of a drive rod 806. The suture passer may be housed within an elongated shaft 808 and may be operated with a drive mechanism included within and actuatable at a handle provided at a proximal end of the shaft.

As shown, the path of the guide elements or needles may diverge, increasing the spacing between the needles beyond the instrument and the amount of tissue purchase thereby. Alternatively, the guide element paths may be parallel or converging as should be apparent to one of skill in the art.

The instrument may employ hollow guides or needles 804 that provide a pathway for passing a suture from outside the abdominal cavity, into the cavity and back out of the cavity. As shown, proximal ends of the needles may be received in corresponding channels 810 of a guide support or tip 812 with a rounded suture guide channel 814 extending between the proximal ends of the needles. This arrangement allows a suture to be fed into the distal end and through one needle, along the guide channel, and into the proximal end and out through the other needle. As shown, the guide channel may have a C-shaped or U-shaped configuration although other channel shapes are contemplated as should be apparent to one of skill in the art.

Figure 20:
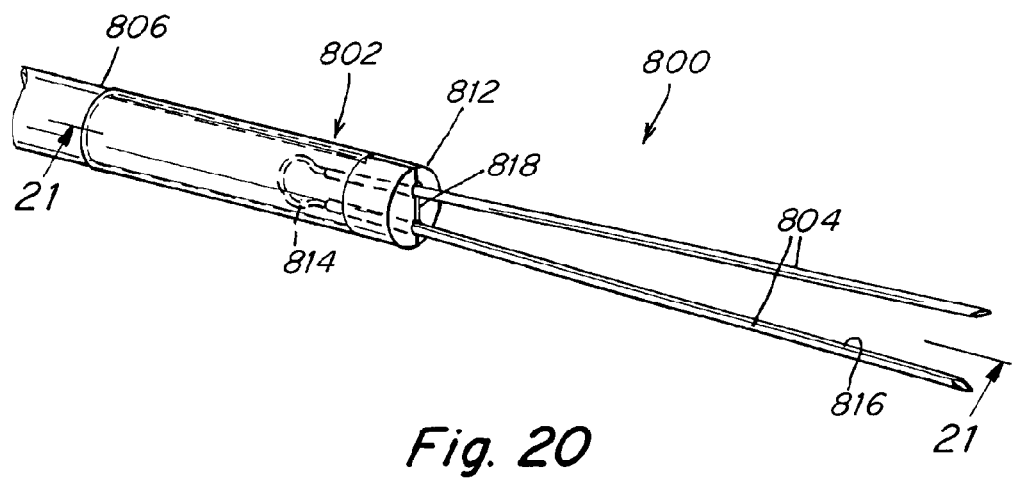
FIGS. 20-23C are illustrations of an instrument for transfascial delivery with a suture guide.
Figure 21:
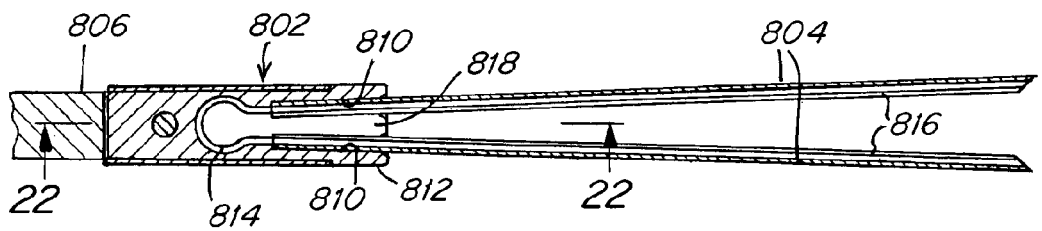
Figure 22:
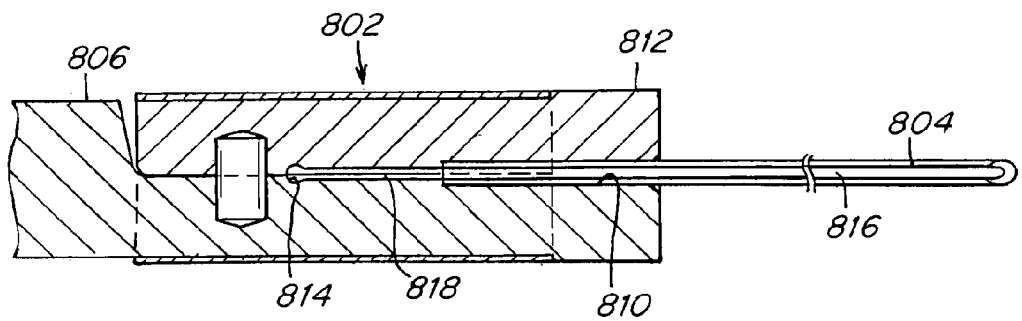

As shown in FIGS. 20-22, the needles may include opposed and inwardly facing slots 816 along their length that align with a release slot 818 located in the guide tip 812 between the proximal ends of the needles to release the suture from the instrument after deployment. It is to be appreciated that the suture passer may employ other features suitable for releasing the suture as should be apparent to one of skill in the art.

Figure 23:
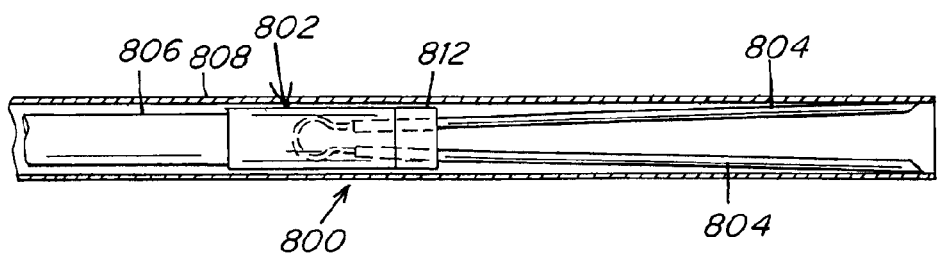
Figure 23A:
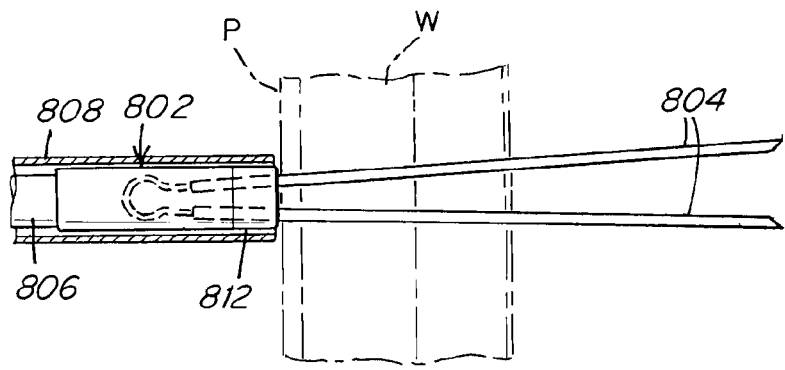

As shown in FIG. 23, the suture passer 802 may be retracted within the shaft 808 for delivery to a desired location within the abdominal cavity. As shown in FIG. 23A, after positioning the instrument adjacent or against the abdominal wall and/or patch, the suture passer 802 may be extended from the shaft 808 to deploy the needles 804 through the patch and/or fascia and further through the skin so that the needles extend outside a patient's body.

Figure 23B:
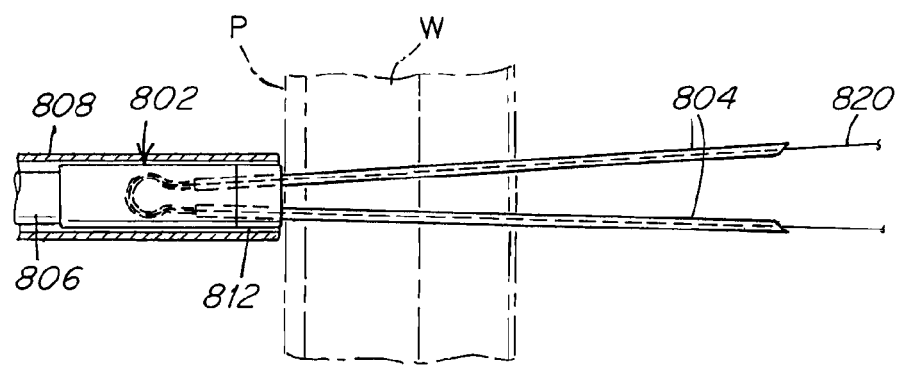

As shown in FIG. 23B, a suture 1420 may be fed through one needle 1404, around the guide channel 1414 and back out the other needle to form a U-shaped suture with both tails of the suture located outside the abdominal cavity. In one embodiment, the suture may be fed through the needles and guide channel using a flexible, yet relatively stiff, leader attached to the leading end of the suture. However, in some applications, a leader may be unnecessary as the suture may be sufficiently stiff to be fed through the suture passer.

Figure 23C:
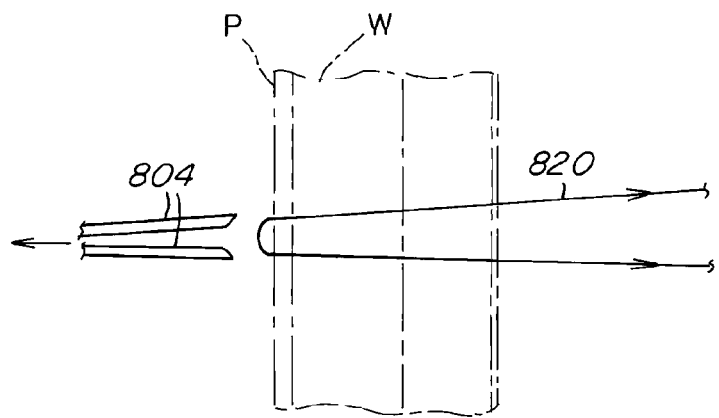

As shown in FIG. 23C, after the suture has been deployed through both needles, the suture may be released from the suture passer through the needle slots 816 and the release slot 818. The suture passer 802 may be withdrawn into the abdominal cavity with the suture extending through the patch and abdominal wall. The suture may be tightened and knotted to secure the patch in position at the abdominal wall.

In one illustrative embodiment shown in FIGS. 24-27, a system 900 for actuating one or more needles or other tissue piercing elements of a delivery instrument, including one or more of the instruments described above, includes a handle body 902 which supports a drive mechanism adapted to actuate one or more needles or other tissue piercing elements in one or more partial strokes. The drive mechanism 904 may include an advancer 906 that is adapted to releasably engage a proximal portion 908 of a needle, a needle drive shaft coupled to one or more needles or other tissue piercing element 910 upon actuation of the drive mechanism to advance the needle in a distal direction relative to an outer shaft 912. A lever 914 is pivotally mounted and includes an upper end 916 coupled to the advancer and a lower end 918 operatively engaged with a trigger 920. As shown, the upper end of the trigger is mounted for pivotal movement with the lower portion of the trigger operatively engaged with the lever.

Figure 27:
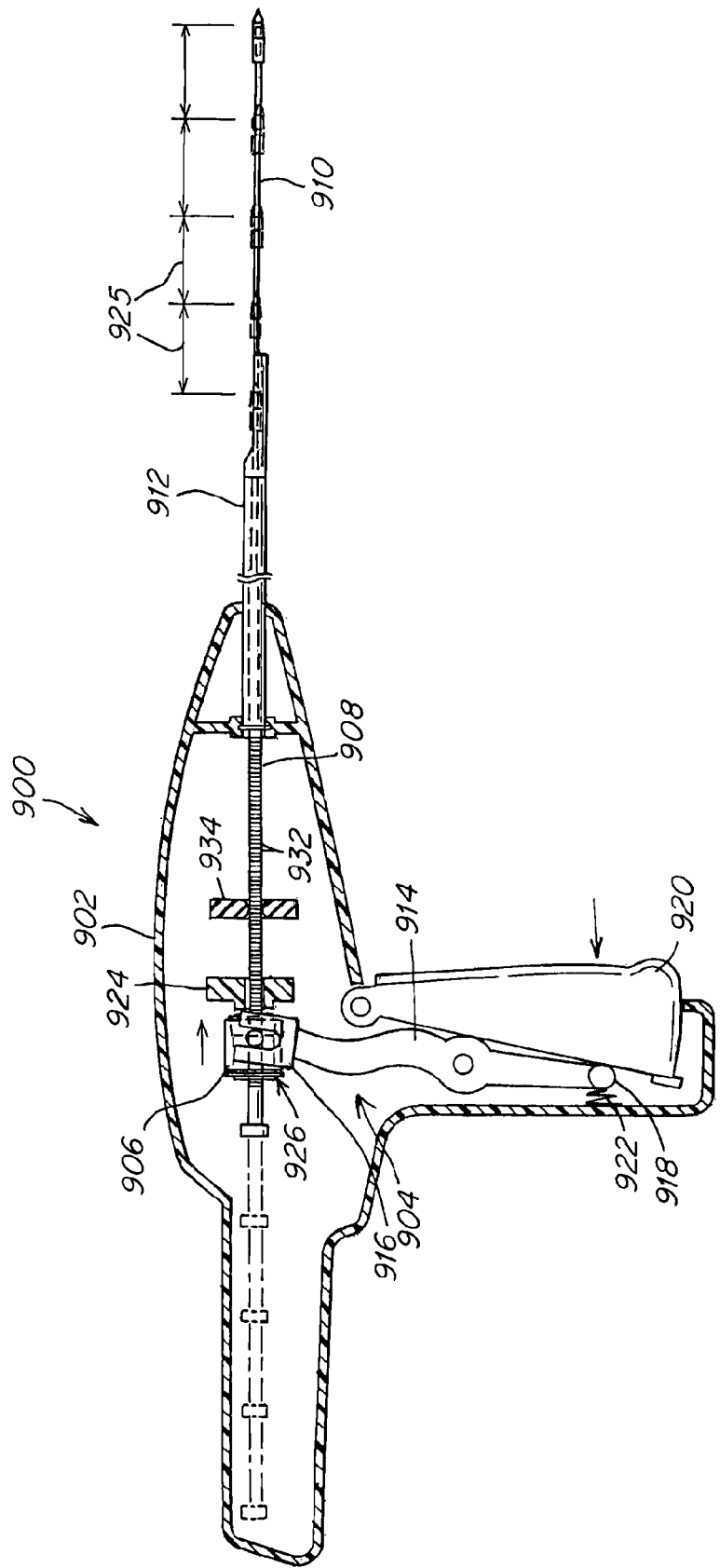

As shown in FIG. 27, the trigger 920 may be pivoted against the biasing force of a spring 922 acting upon the lower end of the lever causing the lever to pivot about its axis with the upper end of the lever moving in the distal direction. The advancer 906, which may be coupled to the lever with a yoke connection, is similarly advanced in the distal direction to drive the needle distally along the shaft. A stop 924 may be provided to engage and limit the distal travel of the advancer corresponding to the desired amount of needle stroke 925 per actuation.

The advancer 906 is adapted to engage the needle or needle drive shaft when the drive mechanism is actuated to advance the needle and to release the needle and slide along a portion of the needle or needle drive shaft when the trigger is released and returns to its initial position under the biasing force of the spring, as shown in FIG. 24. In one embodiment, the advancer 906 may include a clutch 926 adapted to contract inwardly to engage and advance the needle or needle drive shaft when moved in the distal direction and to expand outwardly to release and slide along the needle or needle drive shaft when moved in the proximal direction to reset its position along the needle or drive shaft for a subsequent actuation. The clutch 926 may include a plurality of jaws 928 provided with teeth 930 adapted to engage corresponding teeth 932 provided along the proximal portion of the needle or drive shaft for engaging and advancing the needle. The teeth may be configured to cooperate in a ratcheting manner in which the sets of teeth engage each other to drive the needle beyond a distal end of the outer shaft 912 in response to actuation of the trigger and then release from each other to permit the clutch to slide along the needle or drive shaft and reset for the next actuation. A gripper 2034 may be provided to engage and hold the needle or drive shaft 2010 in position as the drive mechanism is reset.

Figure 28:
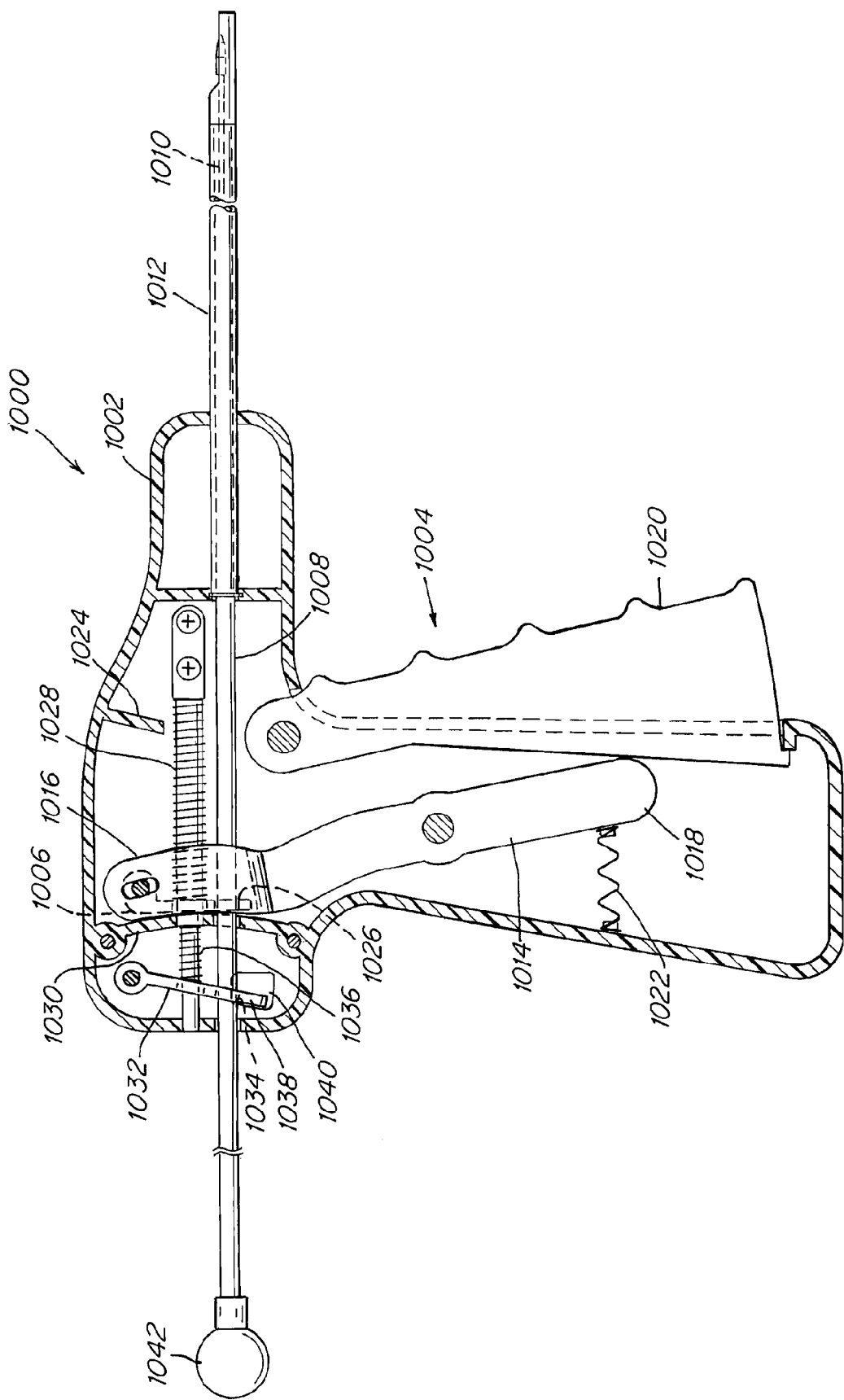
FIGS. 28-29E are partial sectional illustrations of a drive mechanism for an instrument for transfascial delivery of a suture.
Figure 29A:
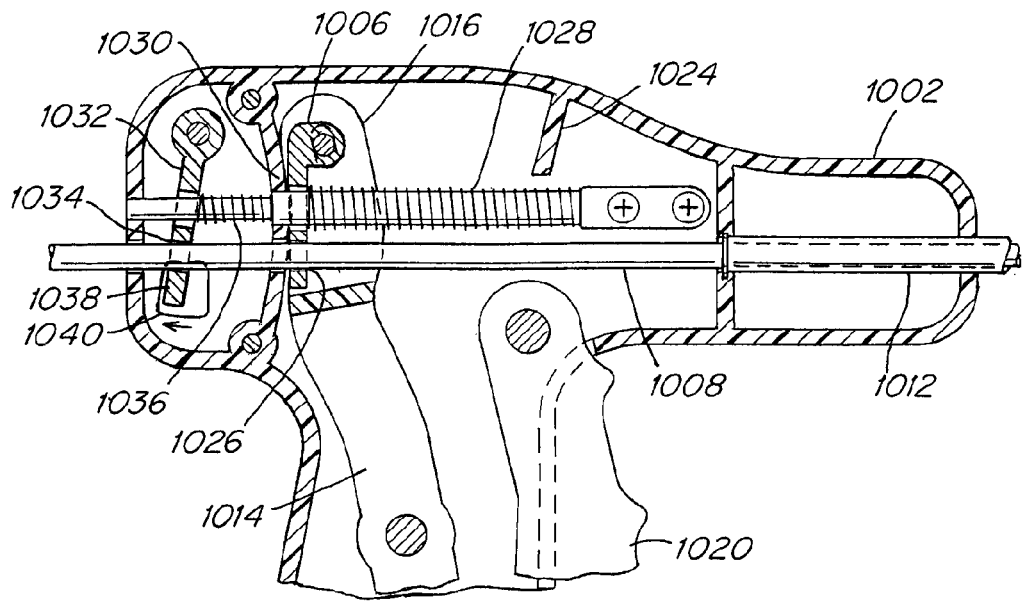
Figure 29B:
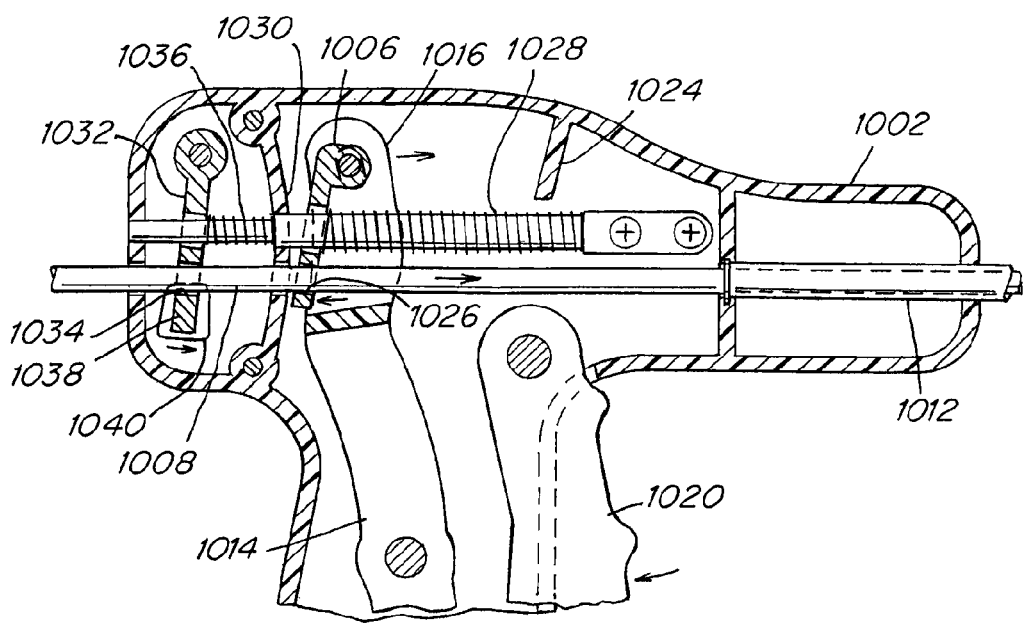
Figure 29C:
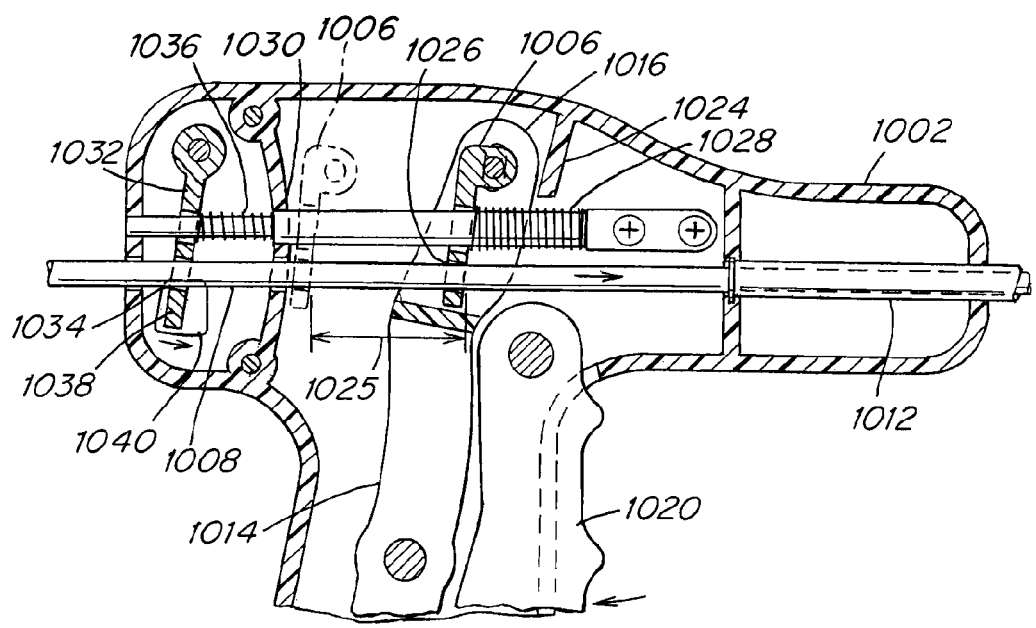
Figure 29D:
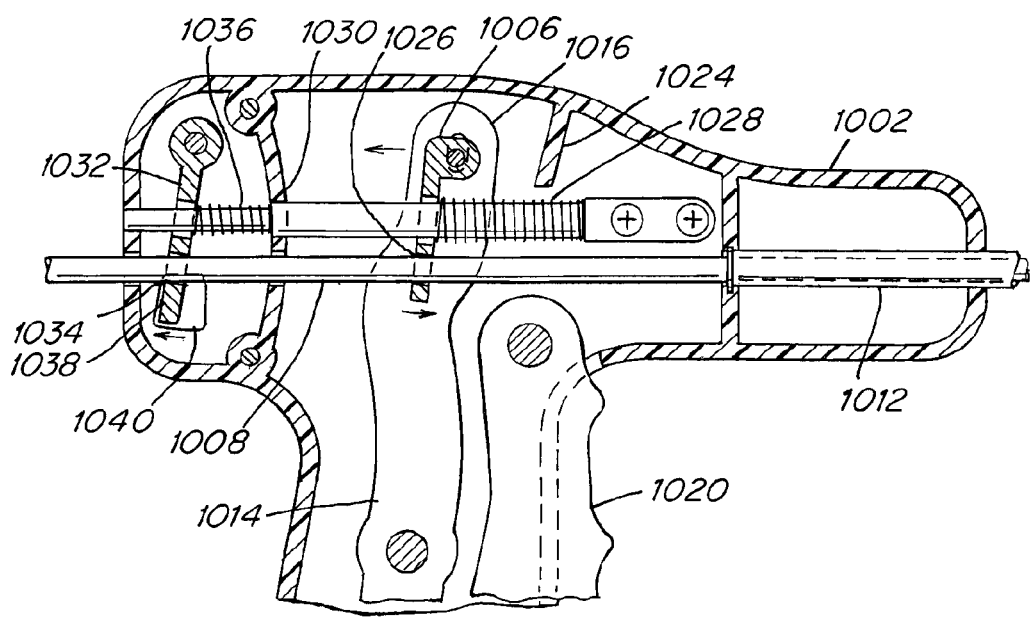
Figure 29E:
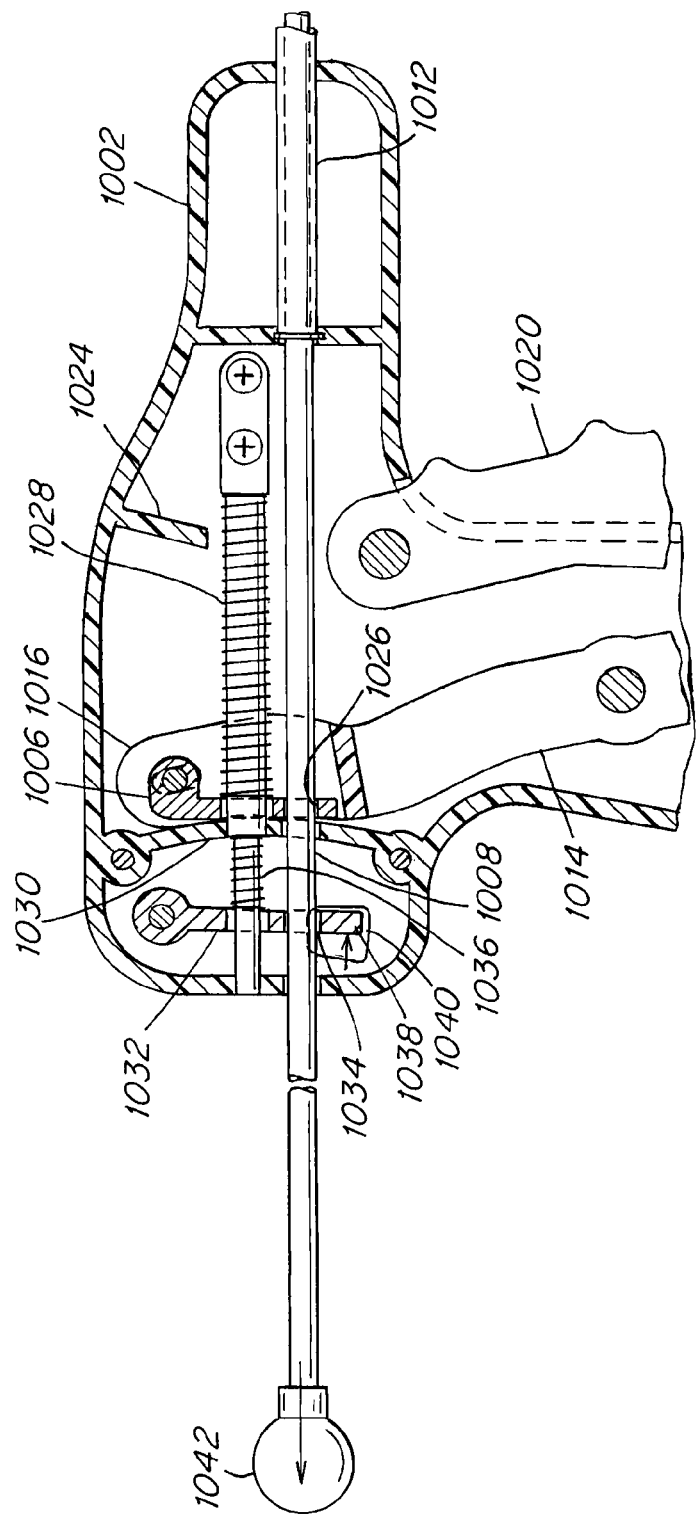

In another illustrative embodiment shown in FIGS. 28-29E, a system 1000 for actuating one or more needles or other tissue piercing elements of a delivery instrument includes a handle body 1002 which supports a drive mechanism adapted to actuate one or more needles or other tissue piercing elements in one or more partial strokes. The drive mechanism 1004 may include an advancer 1006 that is adapted to releasably engage a proximal portion 1008 of a needle, a needle drive shaft coupled to one or more needles or other tissue piercing element 1010 upon actuation of the drive mechanism to advance the needle in a distal direction relative to an outer shaft 1012. An actuation lever 1014 is mounted for pivotal movement and includes an upper end 1016 coupled to the advancer and a lower end 1018 operatively engaged with a trigger 1020. As shown, the upper end of the trigger is mounted for pivotal movement with the lower portion of the trigger operatively engaged with the lever.

As shown in FIG. 28, the trigger 1020 may be pivoted against the biasing force of a spring 1022, such as a compression spring, acting upon the lower end 1018 of the lever causing the lever to pivot about its axis with the upper end 1016 of the lever moving in the distal direction. The advancer 1006 is pivotally mounted to the actuation lever and is similarly advanced in the distal direction to drive the needle distally from the shaft. A first stop 1024 may be provided to engage and limit the distal travel of the upper end of the lever corresponding to the desired amount of needle stroke 1025 per actuation, as shown in FIG. 29C.

The advancer 1006 is adapted to engage the proximal portion 1008 of the needle or needle drive shaft when the drive mechanism is actuated to advance the needle and to release the needle or needle drive shaft and slide along the proximal portion of the needle or drive shaft when the trigger is released and returns to its initial position under the biasing force of the spring 1022, as shown in FIG. 29D. In one embodiment, the advancer 1006 includes an advance lever configured with a clutch-like arrangement in which the advance lever is adapted to pivot in the proximal direction to grip and advance the needle or needle drive shaft when the advancer is moved in the distal direction by the actuation lever, as shown in FIGS. 29B-29C. The advance lever pivots in the opposite or distal direction to release and slide along the needle or drive shaft in the proximal direction to reset its position along the needle or drive shaft for a subsequent actuation.

In one embodiment, the advance lever includes an opening 1026 at its lower end that receives the needle or needle drive shaft and is configured to engage or release the needle or drive shaft in response to the angular position of the advance lever as it pivots relative to the needle or drive shaft. As shown in FIGS. 29B-29C, the advance lever pivots against the biasing force of a spring 1028, such as a compression spring, to engage the needle or drive shaft as the advancer is moved distally during actuation of the lever. A second stop 1030 is provided to abut and hold the advancer out of engagement with the needle or drive shaft prior to actuation or upon reset of the drive mechanism.

The drive mechanism may include a lock 1032 to engage and hold the needle or needle drive shaft in an extended position following each actuation of the device. As shown, the lock is located proximal to the advancer and is adapted to engage and prevent proximal movement of the needle or drive shaft 1010 to reduce inadvertent retraction of the needle from its desired position during a suturing procedure.

In one embodiment, the lock 1032 may include a locking lever configured with a clutch-like arrangement in which the locking lever is pivotally mounted between a locked position (FIG. 29A) to prevent proximal retraction of the needle and a release position (FIG. 29E) to permit proximal retraction. The locking lever includes an opening 1034 at its lower end, similar to the locking lever, that receives the needle or needle drive shaft and is configured to engage or release the needle or drive shaft in response to the angular position of the locking lever as it pivots relative to the needle or drive shaft. The locking lever may be biased to the locked position with a spring 1036, such as a compression spring, located between the second stop 1030 and the lock which applies a biasing force that pivots the locking lever in a proximal direction, as shown in FIG. 29A. Distal movement of the needle or needle drive shaft in response to actuation of the advancer 1006 causes the locking lever 1032 to pivot slightly in the distal direction permitting the needle or drive shaft to be drawn through the lock, as shown in FIGS. 29B-29C. Upon completion of the actuation stroke, the lock 1032 returns to the locked position, as shown in FIG. 29D, to hold the needle in the extended position as the advancer 1006 resets for the next actuation.

As shown in FIG. 29E, the lock 1032 may be released by a user to permit retraction of the needle by manually pushing and pivoting the locking lever in the distal direction against the biasing force of the spring 1036. The lock may be released by pressing against one or more laterally extending tabs 1038 extending from the lower end of the locking lever and through an access opening 1040 in the handle body. The access opening 1040 may be configured to engage the tabs and limit the pivoting of the locking lever. As shown, a knob 1042 may be located at the proximal end of the needle for gripping and retracting the needle, after releasing the lock, to reset the instrument following delivery of a suture.

In one embodiment, a drive mechanism for providing partial needle advancement may be configured to advance the needle in partial strokes of approximately 1.0 inch increments in response to each actuation of the trigger. An instrument employing such a mechanism may be configured to provide a total needle stroke of approximately 4.0 inches. However, it is to be appreciated that the drive mechanism may be configured to provide any amount of partial or incremental needle stroke and the instrument may be configured to provide any amount of total needle stroke as should be apparent to one of skill in the art.

Having described several embodiments of a system for actuating one or more needles or other tissue piercing elements of a delivery instrument, it is to be appreciated that other drive mechanisms are contemplated for actuating a delivery instrument with one or more partial strokes as should be apparent to one of skill in the art. For example, and without limitation, the drive mechanism may include a gear drive, a rack and pinion drive or other suitable drives.

For some transfascial suturing procedures, it may be desirable to identify a desired location for suture placement from outside the abdominal cavity and guide a suturing instrument intra-abdominally to the desired suture location.

Figure 30:
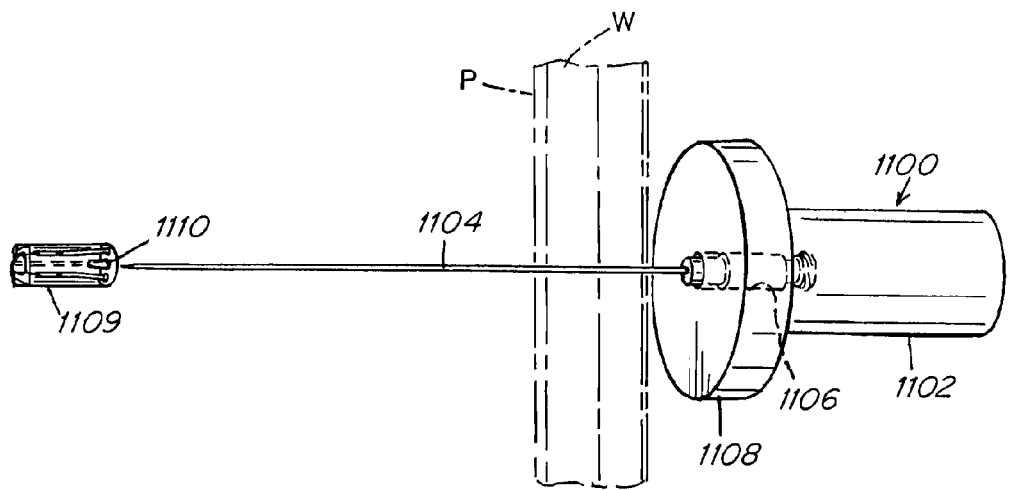
FIGS. 30-30B are illustrations of a guide for positioning an instrument for transfascial delivery of a suture.
Figure 30A:
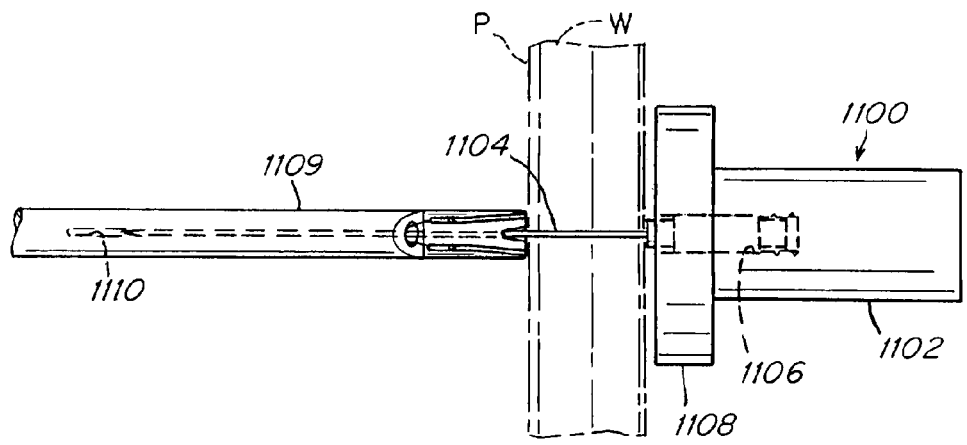
Figure 30B:
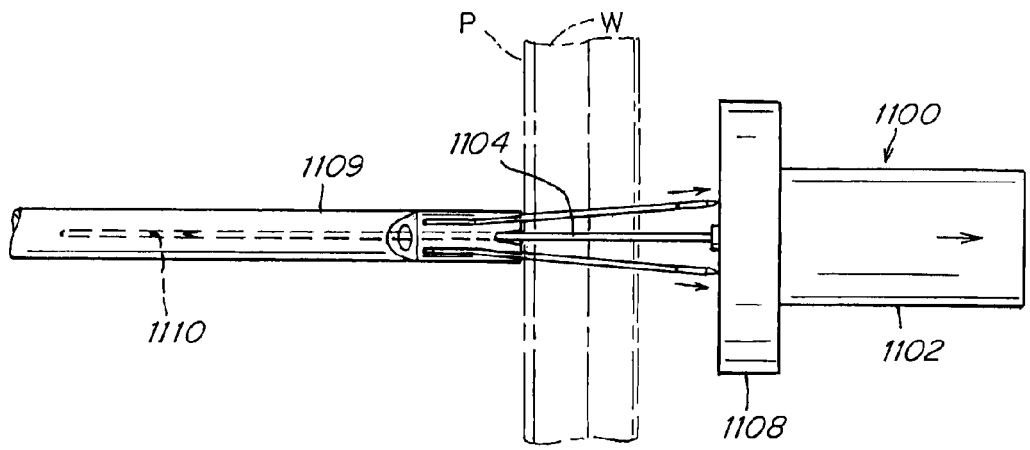

A guide 1100 for transfascial suturing is shown in FIGS. 30-30B and may include a guide handle 1102 and a guide element 1104, which may be in the form of a needle, extending from an end of the handle. In one embodiment, the guide element may include a spinal needle with a luer connector that may be received in a corresponding cavity 1106 provided in the end of the handle. As shown, the handle may include a shield 1108 provided at the base of the handle to protect a user from tissue piercing elements, needles and/or suture retainers that are deployed with a transfascial suturing instrument using an inside-out suturing procedure.

As shown in FIG. 30, the needle 1104 of the suturing guide may be pushed from outside the abdominal cavity, through the skin, fascia and abdominal wall patch and into the abdominal cavity at a desired location and angle. Once the needle has been inserted into the abdominal cavity, an instrument 1109 for delivering a transfascial suture may be delivered to the location of the needle. As shown in FIG. 30A, the needle 1104 may interface with a corresponding feature 1110 provided on the instrument to guide the instrument into position for delivering a suture. In one embodiment, the interface feature may include an elongated channel 1110 configured to receive the needle 1104 and guide the distal end of the instrument into position. However, the instrument may employ any suitable feature to interface with and guide the instrument into position as should apparent to one of skill in the art.

As shown in FIG. 30B, deployment of the needles or other tissue piercing members from the instrument will engage and push the guide 1100 from the skin surface. The spinal needle 1104 may be removed and the suture may be tightened and secured in a manner similar to those described above.

A method of transfascial suturing, for example in the repair of an abdominal wall defect such as a ventral hernia, will now be described. The patient is prepared in the typical fashion for hernia surgery which may include administration of general anesthesia, identification of the hernia size and location, and shaving, washing and sterilization of the surgical site. The abdominal cavity may be insufflated or otherwise expanded to separate the abdominal wall from organs located in the abdominal cavity. A trocar cannula may be inserted to provide camera access to the cavity allowing the physician to visualize the surgical site. A separate laparoscopic cannula may be inserted into the abdominal wall cavity, or an incision (such as formed by a trocar) may be made leading into the abdominal wall cavity, and an abdominal wall repair prosthetic then may be inserted, as described below, through such cannula, incision, or other passageway into the abdominal cavity.

Figure 31:
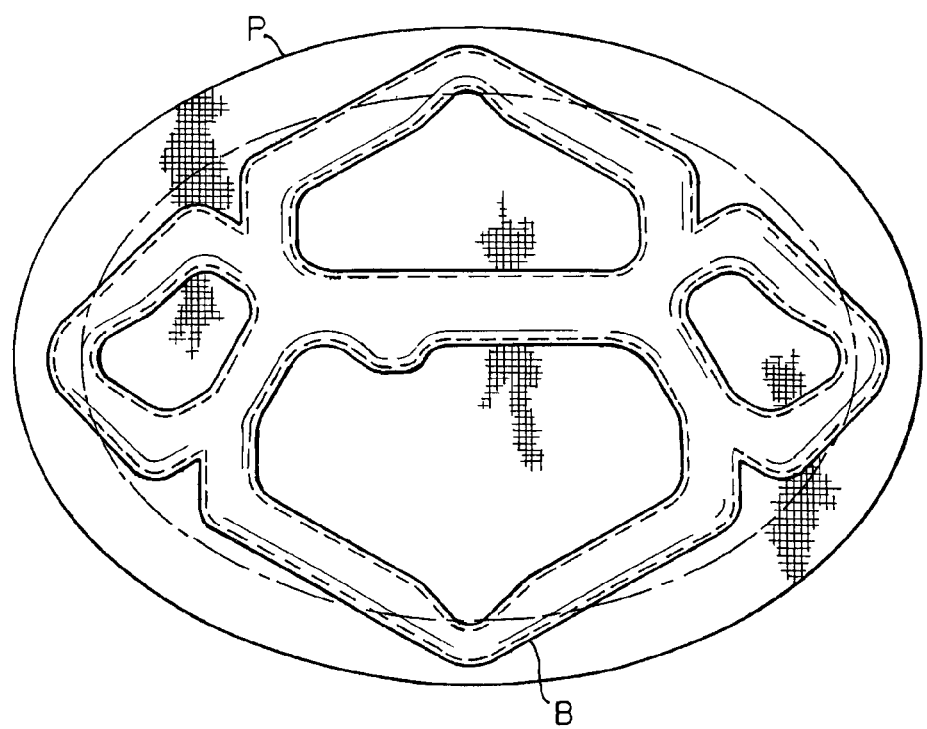
FIG. 31 is an illustration of a ventral repair patch and an inflatable deployment assist device.

The prosthetic, which may be in the form of a patch, preferably is reduced in size to facilitate delivery through the slender cannula or incision. For example, and without limitation, the prosthetic may be rolled, folded, or otherwise collapsed into a shape suitable for passage through the narrow approach to the abdominal cavity. Once located within the cavity, the prosthetic is unfurled or otherwise enlarged, manually or inherently under its own power, and then is positioned relative to the defect, preferably with a margin of at least several centimeters projecting beyond the edges of the defect. Delivery and enlargement of the patch may be facilitated by a mesh introducer such as a PRECISIONPASS instrument available from Davol Inc., assignee of the instant application. Alternatively, a patch deployment assist device, such as an inflatable deployment assist balloon B as illustrated in FIG. 31, may be employed to deliver, expand, and/or position the prosthetic P against the abdominal wall relative to the defect.

In a representative method, the patch P is reduced along with a deflated deployment assist device B, to a slender size such as by rolling the patch and deployment assist device into a cylindrical shape. One or more attachment components on the deployment assist device may help mount the patch to the deployment assist device. An inflation tube for the deployment assist device may be routed through the patch and then grasped, once the deployment assist device and patch are in the abdominal cavity, by a grasper or other instrument that has been inserted into the abdominal cavity from outside of the patient. The grasper is withdrawn, externalizing the inflation tube. The end of the inflation tube outside of the patient may be fluidly connected to an inflation source. Introduction of an inflation medium through the inflation tube will expand the balloon, unfurling the patch into a substantially planar configuration or such other end-use configuration as may be desired. The patch is positioned relative to the defect and when appropriately located, the inflation tube may be pulled from outside of the patient to hoist the deployment assist device and, consequently, the patch carried thereby against the abdominal wall. A hemostat, clamp or other instrument, may be applied to the inflation tube to retain the deployment assist device in position. If desired, the patch still may be rotated to optimize angular orientation of the patch.

The prosthetic patch may be maintained in position against the abdominal wall by the deployment assist device or, alternatively, by use of laparoscopic instruments such as graspers. At this time, in the discretion of the physician, a plurality of coils, tacks, staples, or other mechanical fixation elements may be applied through the patch into the abdominal wall.

A single or twin-needle, or other single or twin-tissue piercing element, instrument for delivering suture is then inserted through the cannula or narrow incision into the abdominal cavity. The instrument may be preloaded with suture or suture may be loaded by the physician or other user. From within the abdominal cavity and under camera visualization, the tip of the suture delivery instrument is placed against a margin of the patch, or other location as desired by the physician. At least one trigger or other control is actuated, from outside of the patient, driving one needle or a pair of needles simultaneously or in a sequence, through the distal end of to the instrument. The needle or needles advance out of the instrument, either in a single full stroke or in partial strokes, and pierce through the patch margin, the abdominal wall (fascia) and, if desired, also through subcutaneous tissue, fat and skin, with the needles delivering suture segments as they travel through the patch and anatomy. Alternatively, an instrument may be employed to extend a needle or other tissue piercing element through the abdominal wall from inside the abdominal cavity to receive a suture from outside the body that is passed into the abdominal cavity at a first location through the abdominal wall, and back out of the cavity at a second location through the abdominal wall.

The tail ends or sections of the suture segments may be retained on the exterior side of the abdominal cavity by application of hemostats, clamps, or other devices, or by grasping by medical staff, to prevent the suture segments from slipping back into the abdominal cavity, as well as to maintain tension on the sutures thereby keeping the patch positioned against the internal abdominal wall. The tail ends or sections external of the abdominal cavity may be pulled to hoist the patch against the abdominal wall and then the hemostats or other instruments applied, or reapplied, to manage the suture ends and patch location. In certain embodiments, suture retainers may be employed to manage the suture tails post deployment.

As the suture is delivered through the fascia, and/or in response to the pulling, external of the abdominal cavity, of the suture tails or segments that have been delivered through the fascia, a suture force distribution member becomes lodged against the prosthetic inside of the abdominal wall cavity. Advantageously, the puncture openings through the patch formed by the needles may be covered, at least in part, by the force distribution member. By covering the puncture openings, the suture force distribution member helps prevent adhesions between the viscera and the tissue infiltratable side of the patch. The delivery of sutures may be repeated, for example at spaced locations about the periphery of the patch, and either after deployment of each suture or after all of the sutures have been delivered, respective suture tail pairs may be knotted, excess suture length trimmed, and the skin over the suture knot closed by stitching, adhesive strip or otherwise.

The deployment assist device may be separated from the patch and removed at any time after proper positioning of the patch, and preferably after the patch has at least been provisionally secured such as by initial suturing or mechanical fixation, and may remain in the abdominal cavity until transfascial suturing has been completed. As mentioned, mechanical fixation elements may, at the discretion of the physician, be applied to the patch prior to transfascial suturing. Alternatively, such mechanical fixation may occur after transfascial suturing, or the transfascial suturing procedure may be concluded without deploying any mechanical fixation elements.

The soft tissue repair prosthetic may be formed of a porous material, such as a knit, woven or non-woven fabric, or may be composed of a solid, substantially non-porous, or microporous material. The prosthesis may be formed of one or more layers of the same or dissimilar material, and the layers may be stacked one on top of the other, side-to-side, or include a combination of both stacking arrangements. The prosthesis may be formed with portions that are tissue infiltratable and other portions that are less tissue infiltratable or are non-tissue infiltratable, providing selected areas of the repair device with different tissue ingrowth and adhesion resistant properties. The prosthesis may be formed of permanent material, resorbable material, or a combination of permanent and resorbable materials. It should be appreciated that the prosthesis may be formed of any biologically compatible material, synthetic or natural, suitable for repairing a tissue or muscle wall defect as would be apparent to one of skill in the art. Depending upon the surgical application, the prosthesis may be in the form of a patch, plug or combination patch and plug.

In a representative embodiment, the soft tissue repair prosthetic is in the form of a ventral hernia repair patch, and may include a tissue infiltratable layer and a barrier layer. The tissue infiltratable layer may include one or more sheets of surgical mesh fabric, such as a polypropylene knit. The barrier layer may be a sheet of synthetic or natural barrier material; for example, and without limitation, a sheet of ePTFE may be stitched, heat fused or otherwise connected to a polypropylene sheet. In the described method of ventral hernia repair, the polypropylene side would face the abdominal wall and the ePTFE side would face the viscera.

Surgical materials which are suitable for tissue or muscle reinforcement and defect correction may be utilized include, but are not limited to, BARD MESH (available from C.R. Bard, Inc.), SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Biologic materials, including XENMATRIX, COLLAMEND, and ALLOMAX (all available from C.R. Bard, Inc.) or COOK SURGISIS (available from Cook Biomedical, Inc.) may also be used. Resorbable materials, including polyglactin (VICRYL—available from Ethicon, Inc.) and polyglycolic acid (DEXON—available from US Surgical, Inc.). These materials may be used alone in a soft tissue repair prosthetic, in combination with one another, or in combination with other materials. The fabric may be formed from multifilament yarns and any suitable method, such as knitting, weaving, braiding, molding and the like, may be employed to form the mesh material. It should be appreciated that when the soft tissue repair prosthesis is in the form of a patch, it may be configured in many shapes, including, but not limited to substantially flat, concave, convex, and concave-convex, and may, for example, be in the shape of a square, rectangle, circle, or ellipse. Further, the patch may be loaded with one or more drugs including, without limitation, an analgesic or antibiotic.

The suture may be formed of a synthetic or natural material, and may be absorbable or non-absorbable. For some applications, the suture may be formed of a stretchable material. Representative suture materials include, but are not limited to, polypropylene, PTFE, nylon, polyester, polybutester, silk, PGA, PLA/PGA, caprolactone, catgut, polyhydroxyalkanoate and PDO.

The above and other aspects of the invention will be appreciated from the detailed description and claims. It should be understood that although aspects of the invention have been described with reference to illustrative embodiments, aspects of the invention are not limited to the embodiments described. Also, aspects of the invention may be used alone, or in any suitable combination with other aspects of the invention.

What is claimed is:

1. A method of delivering a transfascial suture, the method comprising acts of:
    (a) inserting an instrument into an abdominal cavity, the instrument including at least one needle having a sharp distal end adapted to pierce a soft tissue repair prosthetic and abdominal wall tissue;
    (b) passing a suture from outside the abdominal cavity through abdominal wall tissue and into the abdominal cavity at a first location using the instrument from within the abdominal cavity; and
    (c) after act (b), passing the suture from inside the abdominal cavity through abdominal wall tissue and outside the abdominal cavity at a second location spaced from the first location using the instrument from within the abdominal cavity.

2. The method according to claim 1, wherein act (a) includes advancing the at least one needle from inside the abdominal cavity through abdominal wall tissue to position the distal end of the needle outside the abdominal cavity.

3. The method according to claim 2, wherein the at least one needle includes first and second needles adapted to receive a length of suture therethrough, and wherein act (a) includes advancing the first and second needles through abdominal wall tissue at the first and second locations.

4. The method according to claim 3, wherein act (b) includes passing the suture through the first needle and into the abdominal cavity in a direction from the distal end and toward a proximal end of the first needle.

5. The method according to claim 4, wherein act (c) includes passing the suture through the second needle and out of the abdominal cavity in a direction from a proximal end and toward the distal end of the second needle.

6. The method according to claim 5, further comprising, following act (c), an act (d) of releasing the suture from the first and second needles and withdrawing the first and second needles through the abdominal wall and into the abdominal cavity.

7. A method of delivering a transfascial suture, the method comprising acts of:
    (a) inserting a suturing instrument into an abdominal cavity, the suturing instrument including a needle with a sharp end adapted to pierce abdominal wall tissue;
    (b) after act (a), advancing the needle through the abdominal wall at a first location and extending the sharp end of the needle outside the abdominal cavity;
    (c) after act (b), loading a suture on the instrument outside the abdominal cavity; and
    (d) after act (c), drawing the suture through the abdominal wall and into the abdominal cavity at the first location.

8. The method according to claim 7, further comprising, following act (d), an act (e) of advancing the needle and the suture through the abdominal wall at a second location and extending the sharp end of the needle outside the abdominal cavity.

9. The method according to claim 8, further comprising, following act (e), an act of unloading the suture from the instrument outside the abdominal cavity.

10. The method according to claim 7, wherein act (b) includes moving the needle to an extended position beyond a distal end of a shaft of the instrument.

11. The method according to claim 7, wherein act (c) includes loading the suture with a suture catch that is located outside the abdominal cavity.

12. The method according to claim 11, wherein act (c) includes extending the suture catch from a distal end of the instrument and act (d) includes retracting the suture catch into the instrument.

13. The method according to claim 12, further comprising, following act (d), an act of advancing the needle and the suture through the abdominal wall at a second location, extending the sharp end of the needle outside the abdominal cavity, and extending the suture catch from the distal end of the instrument to unload the suture from the instrument outside the abdominal cavity.

14. A method of delivering a transfascial suture, the method comprising acts of:
    (a) inserting a suturing instrument into an abdominal cavity, the suturing instrument including at least one needle with a sharp end adapted to pierce abdominal wall tissue;
    (b) advancing the at least one needle from inside the abdominal cavity through the abdominal wall to outside the abdominal cavity;
    (c) shielding the sharp end of the at least one needle from contact therewith outside the abdominal cavity with the needle extending through the abdominal wall; and
    (d) passing a suture through the abdominal wall with the suturing instrument.

15. The method according to claim 14, wherein act (a) includes inserting the suturing instrument into the abdominal cavity with the sharp end of the at least one needle retracted away from a distal end of the suturing instrument, and act (b) includes extending the sharp end of the at least one needle beyond the distal end of the suturing instrument.

16. The method according to claim 14, wherein the suturing instrument includes an elongated sheath that is extendable beyond the distal end of the suturing instrument, and wherein act (b) includes advancing the at least one needle with the sharp end positioned beyond a distal end of the sheath, and act (c) includes positioning the distal end of the sheath beyond the sharp end of the at least one needle.

17. The method according to claim 15, wherein act (a) includes placing the distal end of the suturing instrument against a soft tissue repair prosthetic and/or the abdominal wall before advancing the needle through a part of the abdominal wall.

18. The method according to claim 14, wherein act (b) includes advancing the at least one needle through a soft tissue repair prosthetic before advancing the needle through a part of the abdominal wall.

19. The method according to claim 14, further comprising, following act (c) and prior to act (d), an act of loading the suturing instrument with the suture outside the abdominal cavity.

20. The method according to claim 14, further comprising, following act (c) and act (d), an act of unloading the suture from the suturing instrument outside the abdominal cavity.

21. A method of delivering a transfascial suture, the method comprising acts of:
- (a) inserting a suturing instrument into an abdominal cavity, the suturing instrument including at least one needle having a sharp end adapted to pierce a soft tissue repair prosthetic and abdominal wall tissue, the suturing instrument adapted to pass a suture through the abdominal wall;
- (b) advancing the at least one needle from inside the abdominal cavity through a portion of the abdominal wall;
- (c) identifying the location of the at least one needle in the abdominal wall via skin tenting and/or skin palpation; and
- (d) following act (c), passing a suture through the abdominal wall with the suturing instrument.

22. The method according to claim 21, further comprising, following act (b), an act (e) of extending a probe beyond the sharp end of the at least one needle and through a portion of the abdominal wall.

23. The method according to claim 22, wherein act (e) includes incrementally advancing the probe through the abdominal wall until the location of the at least one needle is identified via skin tenting and/or skin palpation.

24. The method according to claim 21, wherein act (b) includes incrementally advancing the at least one needle through the abdominal wall until the location of the at least one needle is identified via skin tenting and/or skin palpation.

25. The method according to claim 21, further comprising, following act (c), an act (f) of advancing the at least one needle through the abdominal wall to outside the abdominal cavity.

26. The method according to claim 25, further comprising, following act (f), an act of loading the suturing instrument with the suture outside the abdominal cavity, and wherein act (d) includes passing the suture through the abdominal wall and into the abdominal cavity.

27. The method according to claim 25, further comprising, following act (d) and act (f), an act of unloading the suture from the suturing instrument outside the abdominal cavity.

28. The method according to claim 21, wherein the at least one needle is moveable to at least one extended position beyond a distal end of an elongated shaft of the suturing instrument.

29. The method according to claim 28, wherein act (b) includes moving the at least one needle to the at least one extended position in response to actuation of a drive mechanism.

* * * * *

UNITED STATES PATENT AND TRADEMARK OFFICE
CERTIFICATE OF CORRECTION

| | | |
|---|---|---|
| PATENT NO. | : 9,078,648 B2 | Page 1 of 1 |
| APPLICATION NO. | : 13/290247 | |
| DATED | : July 14, 2015 | |
| INVENTOR(S) | : Donald E. Ziniti et al. | |

It is certified that error appears in the above-identified patent and that said Letters Patent is hereby corrected as shown below:

In the Claims:

At column 26, claim 16, line 45, replace "14" with --15--

Signed and Sealed this
Second Day of February, 2016

Michelle K. Lee
*Director of the United States Patent and Trademark Office*